(12) United States Patent
Martyres et al.

(10) Patent No.: US 8,148,403 B2
(45) Date of Patent: *Apr. 3, 2012

(54) SUBSTITUTED PIPERIDYL-PROPANE-THIOLS

(75) Inventors: Domnic Martyres, Biberach (DE); Matthias Hoffmann, Mittelbiberach (DE); Peter Seither, Biberach (DE); Thierry Bouyssou, Warthausen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 288 days.

This patent is subject to a terminal disclaimer.

(21) Appl. No.: 12/446,001

(22) PCT Filed: Oct. 25, 2007

(86) PCT No.: PCT/EP2007/061455
§ 371 (c)(1),
(2), (4) Date: Jul. 10, 2009

(87) PCT Pub. No.: WO2008/049875
PCT Pub. Date: May 2, 2008

(65) Prior Publication Data
US 2010/0317669 A1    Dec. 16, 2010

(30) Foreign Application Priority Data

Oct. 27, 2006  (EP) .................................. 06123072

(51) Int. Cl.
*A61K 31/445* (2006.01)
*C07D 401/00* (2006.01)
(52) U.S. Cl. ...................... 514/323; 514/222.2; 546/201
(58) Field of Classification Search .................. 514/323, 514/222.2; 546/201
See application file for complete search history.

(56) References Cited

U.S. PATENT DOCUMENTS

| | | | |
|---|---|---|---|
| 6,846,839 B1 * | 1/2005 | Tang et al. | 514/397 |
| 7,759,365 B2 * | 7/2010 | Martyres et al. | 514/323 |
| 2005/0153979 A1 | 7/2005 | Anderskewitz et al. | |
| 2006/0247230 A1 | 11/2006 | Martyres et al. | |

FOREIGN PATENT DOCUMENTS

| | | |
|---|---|---|
| WO | 2004/000831 A1 | 12/2003 |
| WO | 2005/049559 A2 | 6/2005 |
| WO | 2006/117314 A2 | 11/2006 |

OTHER PUBLICATIONS

International Search Report for PCT/EP2007/061455 mailed Feb. 18, 2008.

* cited by examiner

*Primary Examiner* — Rei-tsang Shiao
(74) *Attorney, Agent, or Firm* — Michael P. Morris; Edouard G. Lebel; Usha R. Patel

(57) ABSTRACT

One object of the present invention are novel substituted piperidyl-propane-thiols of the formula (1), wherein $R^1$, $R^2$, $R^3$ and D are defined as below. Another object of the present invention is to provide agonists or antagonists of CCR-3, or pharmaceutically acceptable salts thereof, more particularly to provide pharmaceutical compositions comprising a pharmaceutically acceptable carrier and a therapeutically effective amount of at least one of the compounds of the present invention or a pharmaceutically acceptable salt thereof.

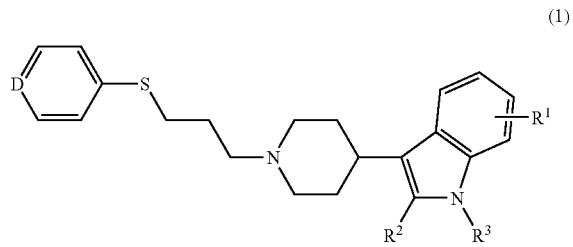

(1)

13 Claims, No Drawings

SUBSTITUTED PIPERIDYL-PROPANE-THIOLS

This application is the national phase entry under 35 U.S.C. §371 of International Application No. PCT/EP2007/061455, filed Oct. 25, 2007, which claims priority to European Application No. EP 06123072.8, filed Oct. 27, 2006, each of which is hereby incorporated by reference in its entirety.

BACKGROUND OF THE INVENTION

1. Technical Field

This invention relates generally to substituted piperidyl-propane-thiols and their use as modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

2. Background Information

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998) and Rollins, Blood, 90, 909-928 (1997)).

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-Ia, MIP-1 (3, the monocyte chemotactic proteins (MCP-1, MCP-2, MCP-3, MCP-4, and MCP-5) and the eotaxins (−1, −2, and −3) are chemotactic for, among other cell types, macrophages, T lymphocytes, eosinophils, mast cells, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, promotion of cell migration, survival and proliferation. There are at least ten human chemokine receptors that bind or respond to CC chemokines with the following characteristic patterns: CCR-1 (or "CKR-1" or "CC-CKR-1") [MIP-Ia, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-Ia, RANTES, MCP-1] (Power et al., J. Biol. Chem., 270, 19495-19500 (1995), Luster, New Eng. J. Med., 338, 436-445 (1998)); CCR-5 (or "CKR-5" OR "CCCKR-5") [MIP-Ia, RANTES, MIP-Ip] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1p] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpes viruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR-4, CCR-2, CCR-3, CCR-5 and CCR-8, can act as coreceptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis, Grave's disease and atherosclerosis. For example, the chemokine receptor CCR-3 is expressed among others on eosinophils, basophils, TH2 cells, alveolar macrophages, mast cells, epithelial cells, microglia cells, astrocytes and fibroblasts. CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR-3 expressing cells by HIV or in preventing the manipulation of immune cellular responses by viruses such as cytomegaloviruses.

Therefore, CCR-3 is an important target and antagonism of CCR-3 is likely to be effective in the treatment of inflammatory, immunoregulatory and infectious disorders and diseases.

BACKGROUND ART

U.S. Pat. No. 5,521,197 discloses piperidine-substituted indoles as 5-HT1F agonists.

The international patent application WO 98006402 discloses the use of these compounds for the treatment of cold or allergic rhinitis.

WO 98011895 discloses these compounds for the treatment of migraine.

Similar compounds are disclosed by WO 2001043740 also used as 5-HT modulators.

WO 2002008223 discloses piperidine-substituted indoles linked to peptide substituted aryl rings as D4 modulators, but also with partially effect at the 5-HT2A or the 5-HT2C receptor.

WO 99037304 discloses substituted piperidine- and piperazine-derivatives for the inhibition of the Factor $X_A$.

WO 2000075130 discloses indoylpiperidine derivatives as antihistaminic and antiallergic agents, what comprises the treatment of bronchial asthma.

The problem underlying the present invention was the provision of novel CCR-3 modulators, preferred with reduced side effects. It has been found surprisingly that certain piperidine-substituted indoles are highly suitable as CCR-3 modulators, having less side effects.

DETAILED DESCRIPTION OF THE INVENTION

The present invention relates to compounds of formula 1,

1

$R^1$ is H, halogen or $OR^{1.1}$;
  $R^{1.1}$ H or $C_{1-6}$-alkyl
$R^2$ is $C_{1-6}$-alkyl, $C_{3-8}$-cycloalkyl, $C(R^{2.1})_2OR^{2.1}$ or $C(R^{2.1})_2N(R^{2.1})_2$;
  $R^{2.1}$ H, $C_{1-6}$-alkyl or $C_{3-8}$-cycloalkyl;
$R^3$ is a group A optionally substituted by one or more $R^{3.1}$;
  A is $C_{3-8}$-cycloalkyl, het or an annelated species of aryl or het;
  $R^{3.1}$ is $C_{1-6}$-alkyl, $COOR^{3.1.2}$, $C_{1-6}$-alkyl-$COOR^{3.1.2}$, $C_{1-6}$-alkyl-COO—$C_{1-6}$-alkyl-$R^{3.1.1}$, $CH_2R^{3.1.1}$, $NHCOR^{3.1.3}$, $CON(R^{3.1.3})_2$, $C_{1-6}$-alkyl-$CON(R^{3.1.3})_2$, COO—$C_{1-6}$-alkyl-$R^{3.1.1}$, $N(R^{3.1.2})_2$, $OR^{3.1.2}$, $NO_2$, $SO_2N(R^{3.1.2})_2$;
    $R^{3.1.1}$ is $NHC_{1-6}$-alkyl, $N(C_{1-6}$-alkyl$)_2$, an aromatic or nonaromatic 5 or 6 membered heterocycle containing one or two atoms selected from the group consisting of nitrogen, oxygen and sulfur, optionally substituted with a carbonyl group;
    $R^{3.1.2}$ is H or $C_{1-6}$-alkyl;
    $R^{3.1.3}$ is H, $C_{1-6}$-alkyl or $C_{3-8}$-cycloalkyl, optionally substituted with halogen, $COOR^{3.1.3.1}$, $COR^{3.1.3.1}$, $R^{3.1.3.1}$, $R^{3.1.3.2}$, $R^{3.1.3.1}R^{3.1.3.2}$, $NR^{3.1.3.1}SO_2R^{3.1.3.2}$, $OR^{3.1.3.1}$, $SR^{3.1.3.1}$, $SOR^{3.1.3.1}$, $SO_2R^{3.1.3.1}$ or $SO_2NR^{3.1.3.1}R^{3.1.3.2}$;
      $R^{3.1.3.1}$ is H, $C_{1-6}$-alkyl or $C_{3-8}$-cycloalkyl;
      $R^{3.1.3.2}$ is H, $C_{1-6}$-alkyl or $C_{3-8}$-cycloalkyl;
D is $CR^4$ or N
$R^4$ is F or H, preferably F;
and pharmaceutically acceptable salts thereof.

Preferred are the above compounds of formula 1, wherein $R^1$ is as shown in the following formula:

Preferred are the above compounds of formula 1, wherein
$R^1$ is H or halogen;
$R^2$ is $C_{1-6}$-alkyl or $C_{3-8}$-cycloalkyl;
$R^3$ is a group A optionally substituted by one or more $R^{3.1}$;
  A is $C_{3-8}$-cycloalkyl, an aromatic or nonaromatic 5 or 6 membered heterocycle containing one or two atoms selected from the group consisting of nitrogen, oxygen and sulfur or an annelated species of aryl or het; preferably $C_{3-8}$-cycloalkyl or an aromatic or nonaromatic 5 or 6 membered heterocycle containing one or two atoms selected from the group consisting of nitrogen, oxygen and sulfur;
  $R^{3.1}$ is $C_{1-6}$-alkyl, $COOR^{3.1.2}$, $C_{1-6}$-alkyl-$COOR^{3.1.2}$, $C_{1-6}$-alkyl-COO—$C_{1-6}$-alkyl-$R^{3.1.1}$, $CH_2R^{3.1.1}$, $NHCOR^{3.1.3}$, $CON(R^{3.1.3})_2$, $C_{1-6}$-alkyl-$CON(R^{3.1.3})_2$, COO—$C_{1-6}$-alkyl-$R^{3.1.1}$, $N(R^{3.1.2})_2$, $OR^{3.1.2}$, $NO_2$, $SO_2N(R^{3.1.2})_2$;
    $R^{3.1.1}$ is $NHC_{1-6}$-alkyl, $N(C_{1-6}$-alkyl$)_2$, an aromatic or nonaromatic 5 or 6 membered heterocycle containing one or two atoms selected from the group consisting of nitrogen, oxygen and sulfur, optionally substituted with a carbonyl group;
    $R^{3.1.2}$ is H or $C_{1-6}$-alkyl;
    $R^{3.1.3}$ is H, $C_{1-6}$-alkyl or $C_{3-8}$-cycloalkyl, optionally substituted with halogen, $COOR^{3.1.3.1}$, $COR^{3.1.3.1}$, $CONR^{3.1.3.1}R^{3.1.3.2}$, $NR^{3.1.3.1}R^{3.1.3.2}$, $NR^{3.1.3.1}SO_2R^{3.1.3.2}$, $OR^{3.1.3.1}$, $SR^{3.1.3.1}$, $SOR^{3.1.3.1}$, $SO_2R^{3.1.3.1}$ or $SO_2NR^{3.1.3.1}R^{3.1.3.2}$;
      $R^{3.1.3.1}$ is H, $C_{1-6}$-alkyl or $C_{3-8}$-cycloalkyl;
      $R^{3.1.3.2}$ is H, $C_{1-6}$-alkyl or $C_{3-8}$-cycloalkyl;
D is $CR^4$ or N
$R^4$ is F or H, preferably F;
and pharmaceutically acceptable salts thereof.

Preferred are the above compounds of formula 1, wherein
$R^1$ is H or halogen;
$R^2$ is $C_{1-6}$-alkyl or $C_{3-8}$-cycloalkyl;
$R^3$ is a group A optionally substituted by one or more $R^{3.1}$;
  A is $C_{3-8}$-cycloalkyl or an aromatic or nonaromatic 5 or 6 membered heterocycle containing one or two atoms selected from the group consisting of nitrogen, oxygen and sulfur;
  $R^{3.1}$ is $NHCOR^{3.1.3}$, $CON(R^{3.1.3})_2$, $C_{1-6}$-alkyl-$CON(R^{3.1.3})_2$;
    $R^{3.1.3}$ is H, $C_{1-6}$-alkyl or $C_{3-8}$-cycloalkyl, optionally substituted with halogen, $COOR^{3.1.3.1}$, $COR^{3.1.3.1}$, $CONR^{3.1.3.1}R^{3.1.3.2}$, $NR^{3.1.3.1}R^{3.1.3.2}$, $NR^{3.1.3.1}SO_2R^{3.1.3.2}$, $OR^{3.1.3.1}$, $SR^{3.1.3.1}$, $SOR^{3.1.3.1}$, $SO_2R^{3.1.3.1}$ or $SO_2NR^{3.1.3.1}R^{3.1.3.2}$;
      $R^{3.1.3.1}$ is H, $C_{1-6}$-alkyl or $C_{3-8}$-cycloalkyl;
      $R^{3.1.3.2}$ is H, $C_{1-6}$-alkyl or $C_{3-8}$-cycloalkyl;
D is $CR^4$ or N, preferably $CR^4$;
$R^4$ is F or H, preferably F;
and pharmaceutically acceptable salts thereof.

Preferred are the above compounds of formula 1, wherein
$R^1$ is H or halogen;
$R^2$ is $C_{1-4}$-alkyl or $C_{3-8}$-cycloalkyl;

$R^3$ is a group A optionally substituted by one or more $R^{3.1}$;
  A is $C_{3-8}$-cycloalkyl or an aromatic or nonaromatic 5 or 6 membered heterocycle containing one or two atoms selected from the group consisting of nitrogen, oxygen and sulfur;
    $R^{3.1}$ is $NHCOR^{3.1.3}$, $CON(R^{3.1.3})_2$, $C_{1-4}$-alkyl-CON$(R^{3.1.3})_2$;
      $R^{3.1.3}$ is H, $C_{1-4}$-alkyl or $C_{3-8}$-cycloalkyl, optionally substituted with halogen, $COOR^{3.1.3.1}$, $COR^{3.1.3.1}$, $CONR^{3.1.3.1}R^{3.1.3.2}$, $NR^{3.1.3.1}R^{3.1.3.2}$, $NR^{3.1.3.1}SO_2R^{3.1.3.2}$, $OR^{3.1.3.1}$, $SR^{3.1.3.1}$, $SOR^{3.1.3.1}$, $SO_2R^{3.1.3.1}$ or $SO_2NR^{3.1.3.1}R^{3.1.3.2}$;
        $R^{3.1.3.1}$ is H, $C_{1-4}$-alkyl or $C_{3-8}$-cycloalkyl;
        $R^{3.1.3.2}$ is H, $C_{1-4}$-alkyl or $C_{3-8}$-cycloalkyl;
D is $CR^4$ or N, preferably $CR^4$;
$R^4$ is F or H, preferably F;
and pharmaceutically acceptable salts thereof.

Preferred are the above compounds of formula 1, wherein
$R^1$ is H or halogen;
$R^2$ is $C_{1-6}$-alkyl, $C_{3-8}$-cycloalkyl;
$R^3$ is a group A optionally substituted by one or more $R^{3.1}$;
  A is $C_{3-8}$-cycloalkyl or an aromatic or nonaromatic 5 or 6 membered heterocycle containing one or two atoms selected from the group consisting of nitrogen, oxygen and sulfur;
    $R^{3.1}$ is $C_{1-6}$-alkyl, $COOR^{3.1.2}$, $C_{1-6}$-alkyl-$COOR^{3.1.2}$, $C_{1-6}$-alkyl-COO—$C_{1-6}$-alkyl-$R^{3.1.1}$, $CH_2R^{3.1.1}$, COO—$C_{1-6}$-alkyl-$R^{3.1.1}$, $N(R^{3.1.2})_2$, $OR^{3.1.2}$, $NO_2$, $SO_2N(R^{3.1.2})_2$;
      $R^{3.1.1}$ is $NHC_{1-6}$-alkyl, $N(C_{1-6}$-alkyl$)_2$, an aromatic or nonaromatic 5 or 6 membered heterocycle containing one or two atoms selected from the group consisting of nitrogen, oxygen and sulfur, optionally substituted with a carbonyl group;
      $R^{3.1.2}$ is H or $C_{1-6}$-alkyl;
D is $CR^4$ or N, preferably $CR^4$;
$R^4$ is F or H, preferably F;
and pharmaceutically acceptable salts thereof.

Preferred are the above compounds of formula 1, wherein
$R^1$ is H or halogen;
$R^2$ is $C_{1-4}$-alkyl, $C_{3-8}$-cycloalkyl;
$R^3$ is a group A optionally substituted by one or more $R^{3.1}$;
  A is $C_{3-8}$-cycloalkyl or an aromatic or nonaromatic 5 or 6 membered heterocycle containing one or two atoms selected from the group consisting of nitrogen, oxygen and sulfur;
    $R^{3.1}$ is $C_{1-4}$-alkyl, $COOR^{3.1.2}$, $C_{1-4}$-alkyl-$COOR^{3.1.2}$, $C_{1-4}$-alkyl-COO—$C_{1-4}$-alkyl-$R^{3.1.1}$, $CH_2R^{3.1.1}$, COO—$C_{1-4}$-alkyl-$R^{3.1.1}$, $N(R^{3.1.2})_2$, $OR^{3.1.2}$, $NO_2$, $SO_2N(R^{3.1.2})_2$;
      $R^{3.1.1}$ is $NHC_{1-4}$-alkyl, $N(C_{1-4}$-alkyl$)_2$, an aromatic or nonaromatic 5 or 6 membered heterocycle containing one or two atoms selected from the group consisting of nitrogen, oxygen and sulfur, optionally substituted with a carbonyl group;
      $R^{3.1.2}$ is H or $C_{1-4}$-alkyl;
D is $CR^4$ or N, preferably $CR^4$;
$R^4$ is F or H, preferably F;
and pharmaceutically acceptable salts thereof.

Particularly preferred are the above compounds of formula 1, wherein
$R^1$ is H or halogen;
$R^2$ is $C_{1-6}$-alkyl or $CH_2O$—$C_{1-6}$-alkyl;
$R^3$ is a group A optionally substituted by one or more $R^{3.1}$;
  A is $C_{3-8}$-cycloalkyl or an aromatic or nonaromatic 5 or 6 membered heterocycle containing one or two nitrogen atoms;
    $R^{3.1}$ is $C_{1-6}$-alkyl, $COOR^{3.1.2}$, $C_{1-6}$-alkyl-$COOR^{3.1.2}$, $CH_2R^{3.1.1}$, CONH—$C_{1-6}$-alkyl-$R^{3.1.1}$, COO—$C_{1-6}$-alkyl-$R^{3.1.1}$, OH, O—$C_{1-6}$-alkyl, $NO_2$, $SO_2N(R^{3.1.2})_2$;
      $R^{3.1.1}$ is $NHC_{1-6}$-alkyl, $N(C_{1-6}$-alkyl$)_2$, an aromatic or nonaromatic 5 or 6 membered heterocycle containing one or two nitrogen atoms optionally substituted with a carbonyl group;
      $R^{3.1.2}$ is H or $C_{1-6}$-alkyl;
$R^{3.2}$ is H or $C_{1-6}$-alkyl;
D is $CR^4$ or N, preferably $CR^4$;
$R^4$ is F;
and pharmaceutically acceptable salts thereof.

Preferred are the above compounds of formula 1, wherein
$R^1$ is H or halogen;
$R^2$ is $C_{1-4}$-alkyl or $CH_2O$—$C_{1-4}$-alkyl;
$R^3$ is a group A optionally substituted by one or more $R^{3.1}$;
  A is $C_{3-8}$-cycloalkyl or an aromatic or nonaromatic 5 or 6 membered heterocycle containing one or two nitrogen atoms;
    $R^{3.1}$ is $C_{1-4}$-alkyl, $COOR^{3.1.2}$, $C_{1-4}$-alkyl-$COOR^{3.1.2}$, $CH_2R^{3.1.1}$, CONH—$C_{1-4}$-alkyl-$R^{3.1.1}$, COO—$C_{1-4}$-alkyl-$R^{3.1.1}$, OH, O—$C_{1-4}$-alkyl, $NO_2$, $SO_2N(R^{3.1.2})_2$;
      $R^{3.1.1}$ is $NHC_{1-4}$-alkyl, $N(C_{1-4}$-alkyl$)_2$;
      $R^{3.1.2}$ is H or $C_{1-4}$-alkyl;
$R^{3.2}$ is H or $C_{1-4}$-alkyl;
D is $CR^4$ or N, preferably $CR^4$;
$R^4$ is F;
and pharmaceutically acceptable salts thereof.

Preferred are the above compounds of formula 1, wherein
$R^1$ is H or F;
$R^2$ is Et or $CH_2OCH_3$
$R^3$ is a group A optionally substituted by one or more $R^{3.1}$;
  A is $C_{3-8}$-cycloalkyl, pyridinyl or pyrazinyl;
    $R^{3.1}$ is $C_{1-4}$-alkyl, $COOR^{3.1.2}$, $C_{1-4}$-alkyl-$COOR^{3.1.2}$, $CH_2R^{3.1.1}$, CONH—$C_{1-4}$-alkyl-$R^{3.1.1}$, COO—$C_{1-4}$-alkyl-$R^{3.1.1}$, OH, O—$C_{1-4}$-alkyl, $NO_2$, $SO_2N(R^{3.1.2})_2$;
      $R^{3.1.1}$ is $NHC_{1-4}$-alkyl, $N(C_{1-4}$-alkyl$)_2$;
      $R^{3.1.2}$ is H or $C_{1-4}$-alkyl;
$R^{3.2}$ is H or $C_{1-4}$-alkyl;
D is $CR^4$ or N, preferably $CR^4$;
$R^4$ is F;
and pharmaceutically acceptable salts thereof.

Preferred are the above compounds of formula 1, wherein
$R^1$ is H or F;
$R^2$ is Et or $CH_2OCH_3$
$R^3$ is a group A optionally substituted by one or more $R^{3.1}$;
  A is $C_{3-8}$-cycloalkyl, pyridinyl or pyrazinyl;
    $R^{3.1}$ is $CH_3$, COOH, COOEt, $CH_2COOH$, $CH_2$ COOEt, $C(CH_3)_2COOH$, $C(CH_3)_2COOMe$, $CH_2R^{3.1.1}$, COO—$CH_2$—$CH_2$—$R^{3.1.1}$, OH, OMe, $NO_2$, $SO_2NMe_2$;
      $R^{3.1.1}$ is $NMe_2$;
D is $CR^4$ or N, preferably $CR^4$;
$R^4$ is F;
and pharmaceutically acceptable salts thereof.

Preferred are the above compounds of formula 1, wherein
$R^1$ is H or F;
$R^2$ is Et or $CH_2OCH_3$
$R^3$ is a group A optionally substituted by one or more $R^{3.1}$;
  A is $C_{3-8}$-cycloalkyl, pyridinyl or pyrazinyl;
    $R^{3.1}$ is $CH_3$, COOH, COOEt, $CH_2R^{3.1.1}$, COO—$CH_2$—$CH_2$—$R^{3.1.1}$, OH, OMe;
      $R^{3.1.1}$ is $NMe_2$;
D is $CR^4$ or N, preferably $CR^4$;
$R^4$ is F;
and pharmaceutically acceptable salts thereof.

Preferred are the above compounds of formula 1, wherein R³ is

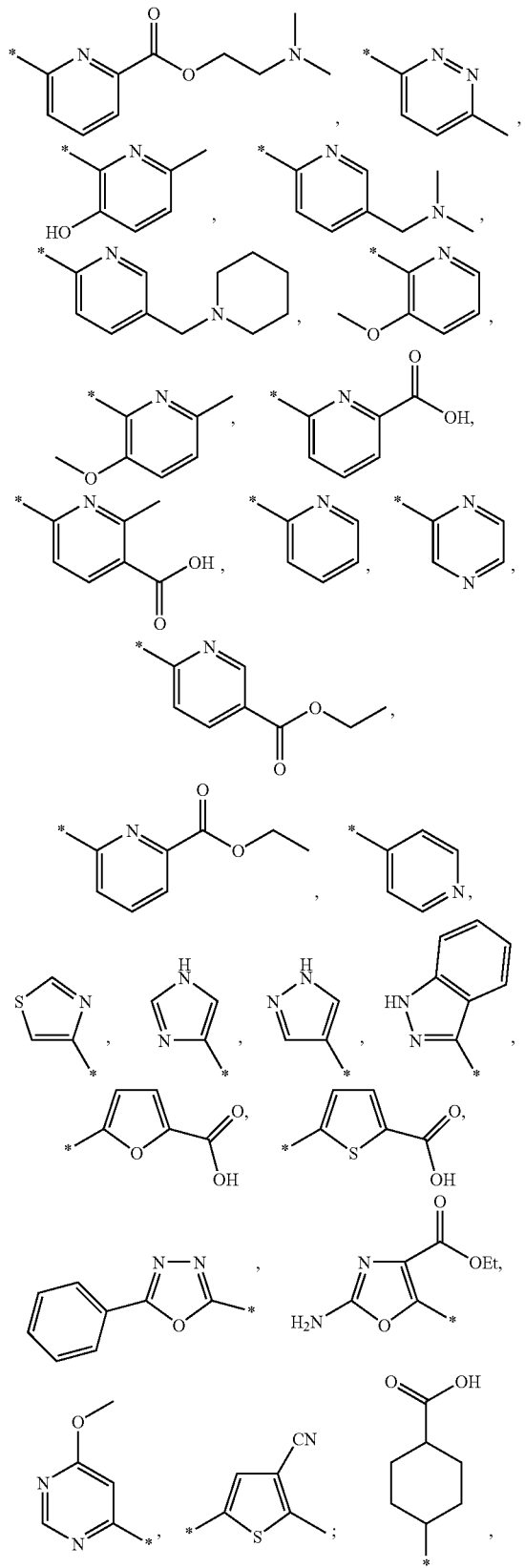

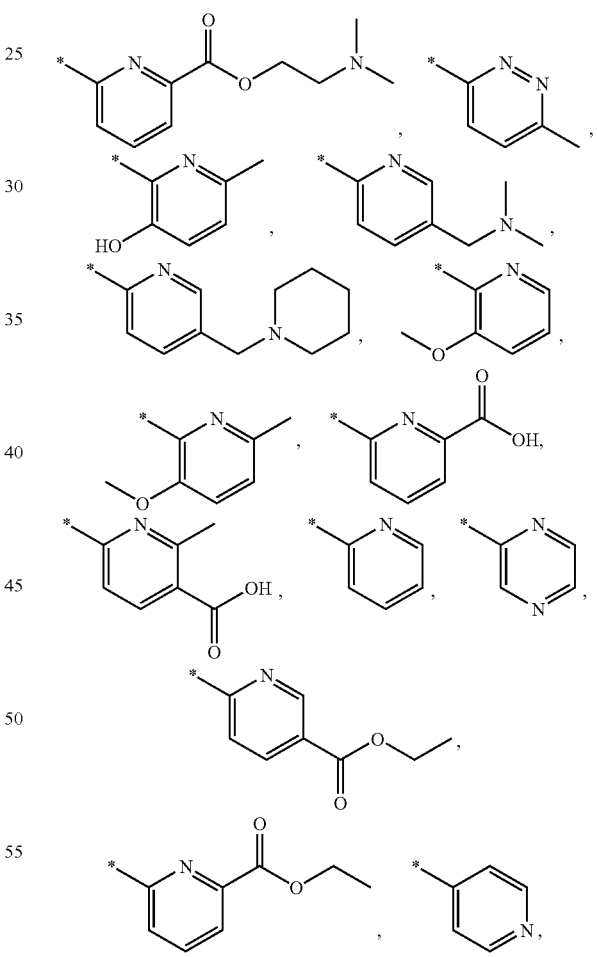

and pharmaceutically acceptable salts thereof.

Preferred are the above compounds of formula 1, wherein R³ is and pharmaceutically acceptable salts thereof.

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$ alkyl means an alkyl group or radical having 1 to 6 carbon atoms. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remingto which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a carboxylic acid, hydroxy, amino, or sulfhydryl group is bonded to any group that, when the prodrug of the present invention is administered to a mammalian subject, it cleaves to form a free carboxylic acid, hydroxyl, free amino, or free sulfhydryl group, respectively. Examples of prodrugs include, but are not limited to, acetate, formate and benzoate derivatives of alcohol and amine functional groups in the compounds of the present invention.

The term "het" as used herein, either alone or in combination with another substituent, means a monovalent substituent derived by removal of a hydrogen from a five-, six- or seven-membered saturated or unsaturated (including aromatic) heterocycle containing carbon atoms and one, two, three or four ring heteroatoms selected from nitrogen, oxygen and sulfur. Examples of suitable heterocycles include: tetrahydrofuran, thiophene, diazepine, isoxazole, piperidine, dioxane, morpholine, piperazine or

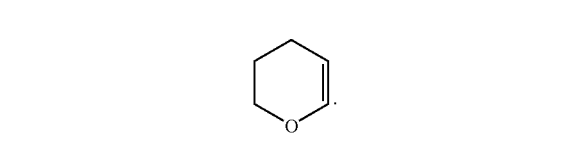

Although generally covered under the term "het", the term "heteroaryl" as used herein precisely defines an unsaturated heterocycle for which the double bonds form an aromatic system. Suitable example of heteroaromatic system include:

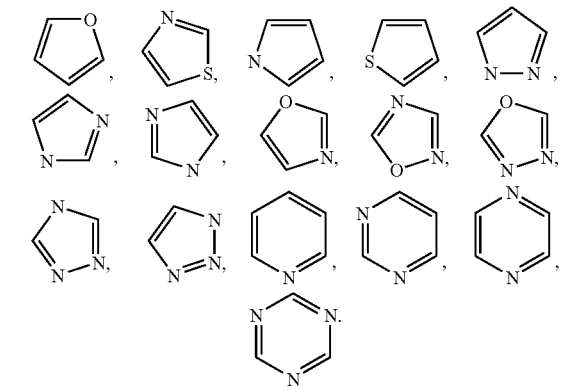

The term "annelated species of aryl or het" as used herein, either alone or in combination with another substituent wherein the annelated species presents as a aryl-het (a), a het-aryl (b) or a het-het (c) annelation means a monovalent substituent derived by removal of one hydrogen from
  an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of a annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1-6}$-alkyl" as used herein, either alone or in combination with another substituent, means acyclic, straight or branched chain alkyl substituents containing from one to six carbon atoms and includes, for example, methyl, ethyl, propyl, butyl, pentyl, hexyl, 1-methylethyl, 1-methylpropyl, 2-methylpropyl or 1,1-dimethylethyl. The term "$C_{1-4}$-alkyl" as used herein, either alone or in combination with another substituent, means acyclic, straight or branched chain alkyl substituents containing from one to four carbon atoms and includes, for example, methyl, ethyl, propyl, butyl, 1-methylethyl, 1-methylpropyl, 2-methylpropyl or 1,1-dimethylethyl.

The term "$C_{3-8}$-cycloalkyl" (including those which are part of other groups) as used herein means cyclic alkyl groups with 3 to 8 carbon atoms, preferred are cyclic alkyl groups with 5 to 6 carbon atoms. Examples include: cyclopropyl, cyclobutyl, cyclopentyl, cyclohexyl, cycloheptyl or cyclooctyl.

The compounds of the instant application are useful for manufacturing a medicament for the prevention and/or treatment of diseases wherein the activity of a CCR-3-receptor is involved.

Preferred is the manufacturing of a medicament for the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

Most preferred is the manufacturing of a medicament for the prevention and/or treatment of e.g. inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs.

Preparation

Synthesis of compounds of the formulae 1a and 1b is described in WO05049559

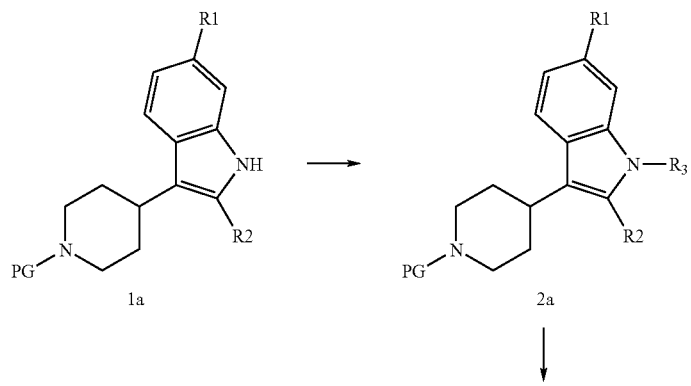

-continued

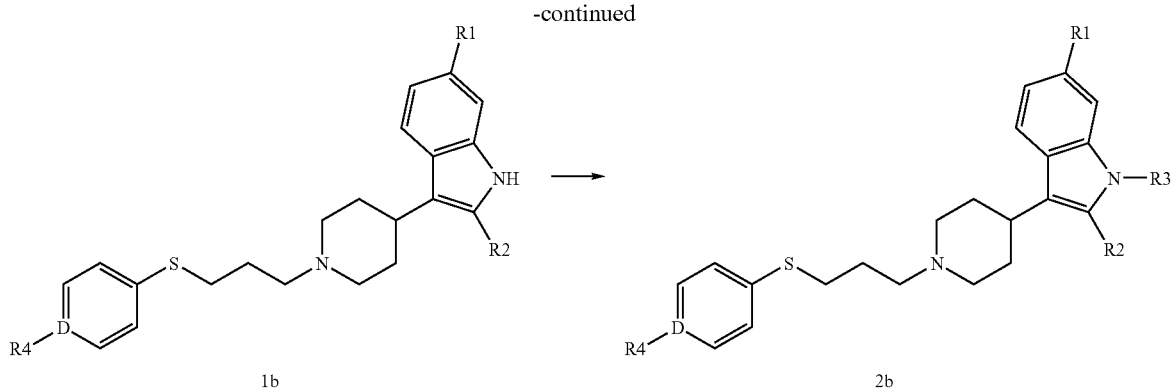

wherein $R^1$, $R^2$, $R^4$, and D are defined as above and PG is a suitable nitrogen protecting group. N-substituted species of the formulae 2a or 2b can be prepared by reacting compounds 1b wherein $R^1$, $R^2$, $R^3$, $R^4$ and D are defined as above. Compound 2b can also be obtained by N-substitution of 1a, deprotecting the reaction product 2a, followed by coupling with compound 3 wherein $R^4$, and D are defined as above and LG is a suitable leaving group.

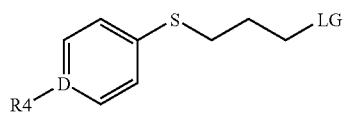

As will be appreciated by one of skill in the art, numerous modifications and variations of the present invention are possible in light of the above teachings. It is therefore to be understood that within the scope of the appended claims, the invention may be practiced otherwise than as specifically described herein.

The following conditions as denoted by "E" or "C" below were used for HPLC-MS analysis:

Method E: HP1100 HPLC-MS;
Mobile Phases:
A: Water with 0.10% HCOOH
B: Acetonitrile with 0.10% HCOOH

| time in min | % A | % B | Flow rate in ml/min |
| --- | --- | --- | --- |
| 0.00 | 90 | 10 | 1.50 |
| 4.50 | 10 | 90 | 1.50 |
| 5.00 | 10 | 90 | 1.50 |
| 5.50 | 90 | 10 | 1.50 |

Stationary phase: Merck Chromolith™ Flash column RP-18e, 4.6 mm×50 mm
The diodearray detection was performed in the range 210-400 nm.
Method C: Waters ZMD, Alliance 2690/2695 HPLC, Waters 2700 Autosampler, Waters 996/2996 Diodearray detector;
Mobile Phases:
A: Water with 0.10% TFA
B: Acetonitrile with 0.10% TFA

| time in min | % A | % B | Flowrate in ml/min |
| --- | --- | --- | --- |
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

Stationary phase: Merck Chromolith™ Flash column RP-18e, 4.6 mm×25 mm
The diodearray detection was performed in the range 210-400 nm.

Example 1

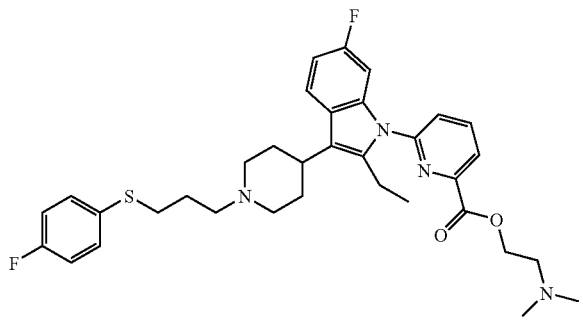

To a solution of 6-(2-ethyl-6-fluoro-3-{1-[3-(4-fluorophenylsulfanyl)-propyl]-piperidin-4-yl}-indol-1-yl)pyridine-2-carboxylic acid (0.19 g) in DCM (2 ml) at r.t., is added oxalylchloride (0.5 ml), under ice cooling is dimethylaminoethanol (1 ml) added. Ethyl acetate is used to extract the organic components and the organic layer is washed with water, dried over $MgSO_4$ and concentrated in vacuo. High performance liquid chromatography is used to provide 54 mg pure product, R.t. 2.56 $min^E$.

The above procedure is used for the conversion of compounds in which $R^{3.1}$ contains $CO_2R^{3.1.2}$ and $R^{3.1.2}$ is H to compounds in which $R^{3.1}$ contains $COO-C_{1-6}$-alkyl-$R^{3.1.1}$ and $R^{3.1.1}$ is $N(CH_3)_2$.

Example 3

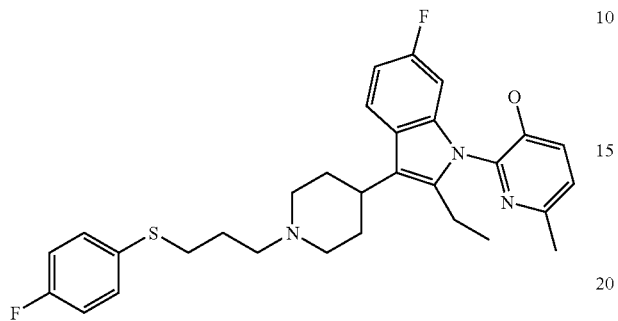

To a solution of 2-ethyl-6-fluoro-3-{1-[3-(4-fluorophenylsulfanyl)-propyl]-piperidin-4-yl}-indol-1-(3-methoxy-6-methyl-pyridine-2-yl)-1H-indole (0.12 g) in DCM (0.5 ml) at r.t., is added borontribromide (1M in DCM, 1344 µl) slowly. Nitrogen is bubbled through the resulting suspension until a orange solid remains. This is dissolved in DCM, and 1M HCl (aq) added under stirring. The organic layer is separated, washed with water, dried over $MgSO_4$ and concentrated in vacuo to yield 105 mg product. Mp. 142° C.

The above procedure is used for the conversion of compounds in which $OR^{3.1.2}$ is $CH_3$ to compounds in which $OR^{3.1.2}$ is H.

Example 6

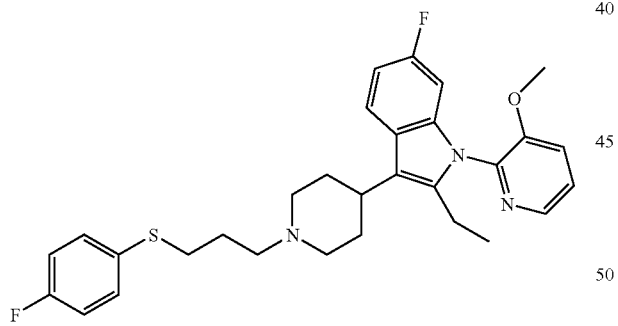

To a solution of 2-ethyl-6-fluoro-3-{1-[3-(4-fluoro-phenylsulfanyl)-propyl]-piperidin-4-yl}-1H-indole (0.12 g) in degassed toluene (2 ml) at r.t., is added potassium phosphate (0.15 g), copper iodide (10 mg), 2-iodo-3-methoxypyridine (63 mg) and N,N''-dimethylcyclohexane-1,2-diamine (4 mg). The mixture is heated at reflux for up to 3 days. Thereafter the mixture is allowed to cool to r.t., and water added. DCM is used to extract the organic components and the organic layer is washed with water, dried over $MgSO_4$ and concentrated in vacuo. High performance liquid chromatography is used to provide 54 mg pure product as a light yellow solid. R.t. 3.24 $min^E$.

All other Ullmann couplings were similarly performed for compounds in which $R^3$ is a group A and A is het or an annelated species of aryl or het, optionally substituted by one or more $R^{3.1}$ as described above.

If iodoaryls were not available, purchasable chloroaryls or bromoaryls were converted to iodoaryls according to Eur. J. Org. Chem. 2002, 1481-4184 and J. Am. Chem. Soc. 2002, 124, 14844-14845 respectively.

When $R^{3.1}$ contains $CO_2R^{3.1.2}$ and $R^{3.1.2}$ is H, the Ullmann coupling was conducted from the purchasable alkyl ester. This ester was subsequently saponified according to the following procedure for example 8.

Example 8

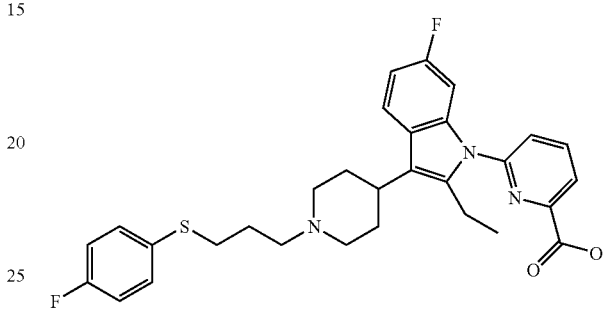

To a solution of 6-(2-ethyl-6-fluoro-3-{1-[3-(4-fluorophenylsulfanyl)-propyl]-piperidin-4-yl}-indol-1-yl)pyridine-2-carboxylic acid (248 mg), in THF (5 ml) is added NaOH (4M, 1.2 ml) and the reaction stirred at r.t. After 3 days this is made slightly acidic with HCl (aq, 2M). DCM is added and the resulting suspension filtered. To the filtrate is added water causing further precipitation which is again filtered. The solid collected is washed with cold acetone-water mixture and dried yielding 158 mg pure product. M p 292° C.

Example 25

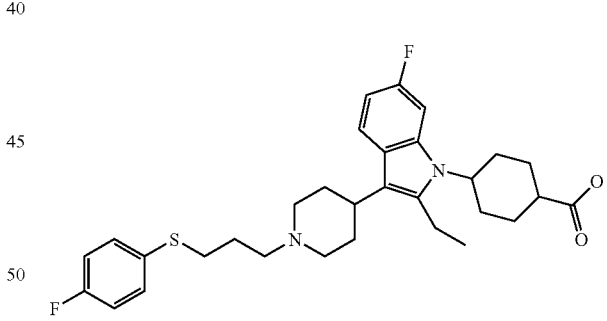

To a stirred solution of 4-fluoro-2-iodoaniline and (18 g) 4-oxo-cyclohexanecarboxylic acid ethyl ester (20 g) in DCM (200 ml) is added acetic acid (4.4 ml) and 4 Å molecular sieves (5 g). After 2 h at rt, sodium acetoxyborohydride (50 g) is added and the suspension stirred overnight. The reaction is made slightly alkaline with KHCO3/NaHCO3(aq) and extracted with DCM to give crude 4-(4-fluoro-2-iodo-phenylamino)-cyclohexanecarboxylic acid ethyl ester.

A portion (30.2 g) of this product is dissolved in THF (50 ml) under argon. To this is added PdCl2(PPh3)2 (3 g) and CuI (1 g). Further is triethylamine (33 ml) added followed by 1 butyne (8.9 g). This is stirred overnight at rt. The reaction is then diluted with MTBE and filtered. The filtrate is concentrated in vacuo and the resulting solid triturated with n-heptane leaving 27 g of crude 4-(2-but-1-ynyl-5-fluoro-phenylamino)-cyclohexanecarboxylic acid ethyl ester. A portion (0.5 g) of this product is made to undergo a ring closure to 4-(2-ethyl-6-fluoro-indol-1-yl)-cyclohexanecarboxylic acid on addition of sodium ethoxide (0.22 g) in NMP (5 ml) after overnight stirring at rt under argon, giving 0.2 g product after flash chromatography (95:5 DCM: MeOH). This intermediate is converted to the compound of example 25 according to the scheme for compounds of the general formula 2a described above.

The above procedure can be used as an alternative to that described above for the conversion of compounds 2b in which A is het or an annelated species of aryl or het, but is required for the conversion of compounds 2b in which A is $C_{3-8}$-cycloalkyl.

The following examples can be synthesised according to the above mentioned synthetic routes.

TABLE 1

EX1

[Structure: R4-phenyl-S-(CH2)3-N-piperidine-indole with R1, R2, R3 substituents]

Examples according to formula EX1

| # | $R^1$ | $R^2$ | $R^3$ | $R^4$ | HPLC Rt[min] | mp [° C.] |
|---|---|---|---|---|---|---|
| 1. | F | $CH_2CH_3$ | [6-pyridyl-C(O)O-CH2CH2-N(CH3)2] | F | $2.56^E$ | |
| 2. | F | $CH_2CH_3$ | [6-methylpyridazin-3-yl] | F | $4.47^E$ | |
| 3. | F | $CH_2CH_3$ | [3-hydroxy-6-methylpyridin-2-yl] | F | | 142 |
| 4. | F | $CH_2CH_3$ | [5-((dimethylamino)methyl)pyridin-2-yl] | F | $2.42^E$ | |
| 5. | F | $CH_2CH_3$ | [5-(piperidin-1-ylmethyl)pyridin-2-yl] | F | $2.48^E$ | |
| 6. | F | $CH_2CH_3$ | [3-methoxypyridin-2-yl] | F | $3.24^E$ | |
| 7. | F | $CH_2CH_3$ | [3-methoxy-6-methylpyridin-2-yl] | F | $3.40^E$ | |
| 8. | F | $CH_2CH_3$ | [6-carboxypyridin-2-yl] | F | $3.10^E$ | |

TABLE 1-continued
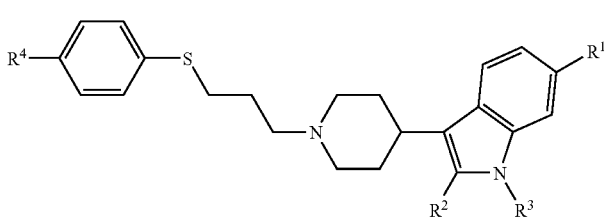
Examples according to formula EX1
| # | R¹ | R² | R³ | R⁴ | HPLC Rt[min] | mp [° C.] |
|---|----|----|----|----|--------------|-----------|
| 9. | F | CH₂CH₃ | 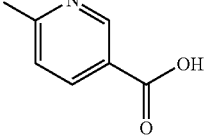 | F | | 292 |
| 10. | F | CH₂CH₃ | 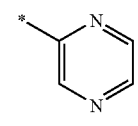 | F | 3.30$^E$ | |
| 11. | F | CH₂CH₃ | 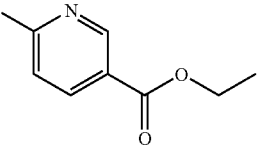 | F | 3.14$^E$ | |
| 12. | F | CH₂CH₃ | 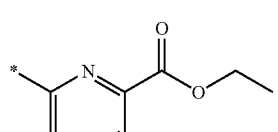 | F | | |
| 13. | F | CH₂CH₃ | 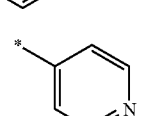 | F | | |
| 14. | F | CH₂CH₃ | 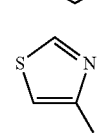 | F | | |
| 15. | F | CH₂CH₃ | 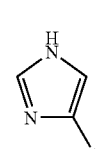 | F | | |
| 16. | F | CH₂CH₃ | 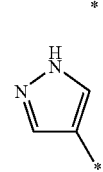 | F | | |
| 17. | F | CH₂CH₃ |  | F | | |

TABLE 1-continued
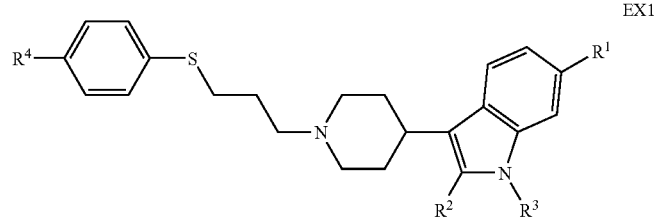
Examples according to formula EX1
| # | R¹ | R² | R³ | R⁴ | HPLC Rt[min] | mp [° C.] |
|---|---|---|---|---|---|---|
| 18. | F | CH₂CH₃ | 1H-indazol-3-yl | F | | |
| 19. | F | CH₂CH₃ | 5-carboxyfuran-2-yl | F | | |
| 20. | F | CH₂CH₃ | 5-carboxythiophen-2-yl | F | | |
| 21. | F | CH₂CH₃ | 5-phenyl-1,3,4-oxadiazol-2-yl | F | | |
| 22. | F | CH₂CH₃ | 2-amino-4-ethoxycarbonyloxazol-5-yl | F | | |
| 23. | F | CH₂CH₃ | 6-methoxypyrimidin-4-yl | F | | |
| 24. | F | CH₂CH₃ | 3-cyanothiophen-5-yl | F | | |
| 25. | F | CH₂CH₃ | 4-carboxycyclohexyl | F | | |

TABLE 1-continued

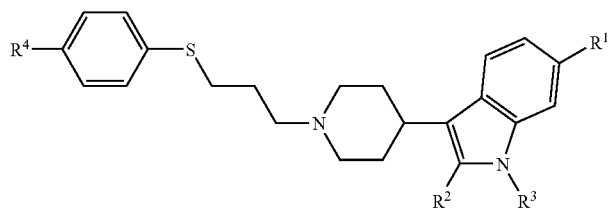

EX1

Examples according to formula EX1

| # | R¹ | R² | R³ | R⁴ | HPLC Rt[min] | mp [° C.] |
|---|----|----|----|----|--------------|-----------|
| 26. | F | $CH_2CH_3$ | 3-carboxycyclohexyl | F | | |
| 27. | F | $CH_2CH_3$ | 3-carboxycyclopentyl | F | | |
| 28. | F | $CH_2CH_3$ | 6-carboxypyridazin-3-yl | F | | |
| 29. | F | $CH_2CH_3$ | 6-hydroxypyridin-3-yl | F | | |

Method of Treatment

Accordingly, the present invention is directed to compounds which are useful in the prevention and/or treatment of a wide variety of inflammatory, infectious, and immunoregulatory disorders and diseases, including asthma and allergic diseases, COPD, infection by pathogenic microbes (which, by definition, includes viruses), as well as autoimmune pathologies such as the rheumatoid arthritis and atherosclerosis, preferred is the prevention and/or treatment of asthma and allergic diseases, COPD, infection by pathogenic microbes, rheumatoid arthritis and atherosclerosis For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, survival or proliferation of CCR-3 expressing cells is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays.

Similarly, an instant compound which promotes one or more functions of the mammalian chemokine receptor (e.g., a human chemokine) as administered to stimulate (induce or enhance) survival or proliferation of CCR-3 expressing cells or an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversushost disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis*, Hookworm, *Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combinations

The compounds of general formula 1 may be used on their own or combined with other active substances of formula 1 according to the invention. The compounds of general formula 1 may optionally also be combined with other pharmacologically active substances. These include, in particular, betamimetics, anticholinergics, corticosteroids, PDE4-inhibitors, LTD4-antagonists, EGFR-inhibitors, dopamin-agonists, antiallergic agents, PAF-antagonists, PI3-kinase inhibitors, MPR4-Inhibitors, iNOS-Inhibitors and SYK-Inhibitors, but also combinations of two or three active substances, i.e.:

Betamimetics with corticosteroids, PDE4-inhibitors, EGFR-inhibitors or LTD4-antagonists, Anticholinergics with betamimetics, corticosteroids, PDE4-inhibitors, EGFR-inhibitors or LTD4-antagonists, Corticosteroids with PDE4-inhibitors, EGFR-inhibitors or LTD4-antagonists PDE4-inhibitors with EGFR-inhibitors or LTD4-antagonists EGFR-inhibitors with LTD4-antagonists.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, CHF-1035, HOKU-81, KUL-1248 and 3-(4-{6-[2-Hydroxy-2-(4-hydroxy-3-hydroxymethyl-phenyl)-ethylamino]-hexyloxy}-butyl)-benzyl-sulfonamide 5-[2-(5,6-Diethyl-indan-2-ylamino)-1-hydroxy-ethyl]-8-hydroxy-1H-quinolin-2-one 4-Hydroxy-7-[2-{[2-{[3-(2-phenylethoxy)propyl]sulphonyl}ethyl]amino}ethyl]-2(3H)-benzothiazolone 1-(2-Fluoro-4-hydroxyphenyl)-2-[4-(1-benzimidazolyl)-2-methyl-2-butylamino]ethanole 1-[3-(4-Methoxybenzyl-amino)-4-hydroxyphenyl]-2-[4-(1-benzimidazolyl)-2-methyl-2-butylamino]ethanole 1-[2H-5-hydroxy-3-oxo-4H-1,4-benzoxazin-8-yl]-2-[3-(4-N, N-dimethylaminophenyl)-2-methyl-2-propylamino]ethanole 1-[2H-5-hydroxy-3-oxo-4H-1,4-benzoxazin-8-yl]-2-[3-(4-methoxyphenyl)-2-methyl-2-propylamino]ethanole 1-[2H-5-hydroxy-3-oxo-4H-1,4-benzoxazin-8-yl]-2-[3-(4-n-butyloxyphenyl)-2-methyl-2-propylamino]ethanole 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-Hydroxy-8-(1-hydroxy-2-isopropylaminobutyl)-2H-1,4-benzoxazin-3-(4H)-one 1-(4-Amino-3-chloro-5-trifluormethylphenyl)-2-tert.-butylamino)ethanol 6-Hydroxy-8-{1-hydroxy-2-[2-(4-methoxy-phenyl)-1,1-dimethyl-ethylamino]-ethyl}-4H-benzo[1,4]oxazin-3-one 6-Hydroxy-8-{1-hydroxy-2-[2-(4-phenoxy-acetic acid ethylester)-1,1-dimethyl-ethylamino]-ethyl}-4H-benzo[1,4]oxazin-3-one 6-Hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-Dimethyl-2-(2,4,6-trimethylphenyl)-ethylamino]-1-hydroxy-ethyl}-6-hydroxy-4H-benzo[1,4]oxazin-3-one 6-Hydroxy-8-{1-hydroxy-2-[2-(4-hydroxy-phenyl)-1,1-dimethyl-ethylamino]-ethyl}-4H-benzo[1,4]oxazin-3-one 6-Hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-Ethyl-phenyl)-1,1-dimethyl-ethylamino]-1-hydroxy-ethyl}-6-hydroxy-4H-benzo[1,4]oxazin-3-one 8-{2-[2-(4-Ethoxy-phenyl)-1,1-dimethyl-ethylamino]-1-hydroxy-ethyl}-6-hydroxy-4H-benzo[1,4]oxazin-3-one 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-Difluor-phenyl)-1,1-dimethyl-ethylamino]-1-hydroxy-ethyl}-6-hydroxy-4H-benzo[1,4]oxazin-3-on 1-(4-Ethoxy-carbonylamino-3-cyano-5-fluorophenyl)-2-(tert-butylamino)ethanol N-[2-Hydroxy-5-(1-hydroxy-2-{2-[4-(2-hydroxy-2-phenyl-ethylamino)-phenyl]-ethylamino}-ethyl)-phenyl]-formamide 8-Hydroxy-5-(1-hydroxy-2-{2-[4-(6-methoxy-biphenyl-3-ylamino)-phenyl]-ethylamino}-ethyl)-1H-quinolin-2-one 8-Hydroxy-5-[1-hydroxy-2-(6-phenethylamino-hexylamino)-ethyl]-1H-quinolin-2-one 5-[2-(2-{4-[4-(2-Amino-2-methyl-propoxy)-phenylamino]-phenyl}-ethylamino)-1-hydroxy-ethyl]-8-hydroxy-1H-quinolin-2-one

[3-(4-{6-[2-Hydroxy-2-(4-hydroxy-3-hydroxymethyl-phenyl)-ethylamino]-hexyloxy}-butyl)-5-methyl-phenyl]-urea 4-(2-{6-[2-(2,6-Dichloro-benzyloxy)-ethoxy]-hexylamino}-1-hydroxy-ethyl)-2-hydroxymethyl-phenol 3-(4-{6-[2-Hydroxy-2-(4-hydroxy-3-hydroxymethyl-phenyl)-ethylamino]-hexyloxy}-butyl)-benzenesulfonamide 3-(3-{7-[2-Hydroxy-2-(4-hydroxy-3-hydroxymethyl-phenyl)-ethylamino]-heptyloxy}-propyl)-benzenesulfonamide 4-(2-{6-[4-(3-Cyclopentanesulfonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide (R,S)-4-(2-{[6-(2,2-Difluoro-4-phenylbutoxy)hexyl]amino}-1-hydroxy-ethyl)-2-(hydroxymethyl)phenol (R,S)-4-(2-{[6-(2,2-Difluoro-2-phenylethoxy)hexyl]amino}-1-hydroxy-ethyl)-2-(hydroxymethyl)phenol (R,S)-4-(2-{[4,4-Difluoro-6-(4-phenylbutoxy)hexyl]amino}-1-hydroxy-ethyl)-2-(hydroxymethyl)phenol (R,S)-4-(2-{[6-(4,4-Difluoro-4-phenylbutoxy)hexyl]amino}-1-hydroxy-ethyl)-2-(hydroxymethyl)phenol (R,S)-5-(2-{[6-(2,2-Difluoro-2-phenylethoxy)hexyl]amino}-1-hydroxy-ethyl)-8-hydroxyquinolin-2(1H)-one (R,S)-[2-({6-[2,2-Difluoro-2-(3-methylphenyl)ethoxy]hexyl}amino)-1-hydroxyethyl]-2-(hydroxymethyl)phenol 4-(1R)-2-{[6-(2,2-Difluoro-2-phenylethoxy)hexyl]amino}-1-hydroxyethyl)-2-(hydroxymethyl)phenol (R,S)-2-(Hydroxymethyl)-4-(1-hydroxy-2-{[4,4,5l5-tetrafluoro-6-(3-phenylpropoxy)-hexyl]amino}ethyl)phenol (R,S)-[5-(2-{[6-(2,2-Difluoro-2-phenylethoxy)hexyl]amino}-1-hydroxy-ethyl)-2-hydroxyphenyl]formamide (R,S)-4-[2-({6-[2-(3-Bromophenyl)-2,2-difluoroethoxy]hexyl}amino)-1-hydroxyethyl]-2-(hydroxymethyl)phenol (R,S)—N-[3-(1,1-Difluoro-2-{[6-({2-hydroxy-2-[4-hydroxy-3-(hydroxymethyl)phenyl]-ethyl}amino)hexyl]oxy}ethyl)phenyl]urea 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione (R,S)-4-(2-({6-[2,2-difluoro-2-(3-methoxyphenyl)ethoxy]hexyl}amino)-1-hydroxyethyl]-2-(hydroxymethyl)phenol 5-((1R)-2-{[6-(2,2-difluoro-2-phenylethoxy)hexyl]amino}-1-hydroxyethyl)-8-hydroxyquinolin-2(1H)-one 4-((1R)-2-{[4,4-Difluoro-6-(4-phenylbutoxy)hexyl]amino}-1-hydroxy-ethyl)-2-(hydroxymethyl)phenol (R,S)-4-(2-{[6-(3,3-Difluoro-3-phenylpropoxy)hexyl]amino}-1-hydroxy-ethyl)-2-(hydroxymethyl)phenol (R,S)-(2-{[6-(2,2-Difluoro-2-phenylethoxy)-4,4-difluorohexyl]amino}-1-hydroxyethyl)-2-(hydroxymethyl)phenol (R,S)-4-(2-{[6-(2,2-difluoro-3-phenylpropoxy)hexyl]amino}-1-hydroxy ethyl)-2-(hydroxymethyl)phenol optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Furthermore 2,2-Diphenylpropion acid tropenolester-methobromide
2,2-Diphenylpropion acid scopinester-methobromide
2-Fluor-2,2-Diphenylacetic acid scopinester-methobromide
2-Fluor-2,2-Diphenylacetic acid tropenolester-methobromide
3,3',4,4'-Tetrafluorbenzil acid tropenolester-Methobromide
3,3',4,4'-Tetrafluorbenzil acid scopinester-Methobromide
4,4'-Difluorbenzil acid tropenolester-Methobromide
4,4'-Difluorbenzil acid scopinester-Methobromide
3,3'-Difluorbenzil acid tropenolester-Methobromide
3,3'-Difluorbenzil acid scopinester-Methobromide
9-Hydroxy-fluoren-9-carbon acid tropenolester-Methobromide
9-Fluor-fluoren-9-carbon acid tropenolester-Methobromide
9-Hydroxy-fluoren-9-carbon acid scopinester-Methobromide
9-Fluor-fluoren-9-carbon acid scopinester Methobromide
9-Methyl-fluoren-9-carbon acid tropenolester Methobromide
9-Methyl-fluoren-9-carbon acid scopinesterMethobromide
Benzil acid cyclopropyltropinester-Methobromide
2,2-Diphenylpropion acid cyclopropyltropinester-Methobromide
9-Hydroxy-xanthen-9-carbon acid cyclopropyltropinester-Methobromide
9-Methyl-fluoren-9-carbon acid cyclopropyltropinester-Methobromide
9-Methyl-xanthen-9-carbon acid cyclopropyltropinester-Methobromide
9-Hydroxy-fluoren-9-carbon acid cyclopropyltropinester-Methobromide
4,4'-Difluorbenzil acid methylestercyclopropyltropinester-Methobromide
9-Hydroxy-xanthen-9-carbon acid tropenolester-Methobromide
9-Hydroxy-xanthen-9-carbon acid scopinester Methobromide
9-Methyl-xanthen-9-carbon acid tropenolester-Methobromide
9-Methyl-xanthen-9-carbon acid scopinesterMethobromide
9-Ethyl-xanthen-9-carbon acid tropenolester Methobromide
9-Difluormethyl-xanthen-9-carbon acid tropenolester-Methobromide
9-Hydroxymethyl-xanthen-9-carbon acid scopinester-Methobromide Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, RPR-106541, NS-126 and 6,9-Difluoro-17-[(2-furanylcarbonyl)oxy]-11-hydroxy-16-methyl-3-oxo-androsta-1,4-dien-17-carbothion acid (S)-fluoromethylester
6,9-Difluoro-11-hydroxy-16-methyl-3-oxo-17-propionyloxy-androsta-1,4-dien-17-carbothion acid (S)-(2-oxo-tetrahydro-furan-3S-yl)ester,
6α,9α-difluoro-11β-hydroxy-16α-methyl-3-oxo-17α-(2,2,3,3-tertamethylcyclopropylcarbonyl)oxy-androsta-1,4-diene-17β-carboxylic acid cyanomethyl ester optionally in racemic form, as enantiomers, diastereomeres or as pharmacologically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibitors which may be mentioned include Enprofylline, Theophylline, Roflumilaste, Ariflo (Cilomilast), Tofimilaste, Pumafentrine, Lirimilaste, Arofylline, Atizorame, Oglemilastum, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and
N-(3,5-Dichloro-1-oxo-pyridin-4-yl)-4-difluormethoxy-3-cyclopropylmethoxybenzamide
(−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamid
(R)-(+)-1-(4-Bromobenzyl)-4-[(3-cyclopentyloxy)-4-methoxyphenyl]-2-pyrrolidon
3-(Cyclopentyloxy-4-methoxyphenyl)-1-(4-N'-[N-2-cyano-S-methyl-isothioureido]benzyl)-2-pyrrolidone
cis[4-Cyano-4-(3-cyclopentyloxy-4-methoxyphenyl)cyclohexan-1-carbon acid]
2-carbomethoxy-4-cyano-4-(3-cyclopropylmethoxy-4-difluoromethoxyphenyl)cyclohexan-1-one
cis[4-Cyano-4-(3-cyclopropylmethoxy-4-difluoromethoxyphenyl)cyclohexan-1-ol]
(R)-(+)-Ethyl[4-(3-cyclopentyloxy-4-methoxyphenyl)pyrrolidin-2-yliden]acetate
(S)-(−)-Ethyl[4-(3-cyclopentyloxy-4-methoxyphenyl)pyrrolidin-2-yliden]acetate
9-Cyclopentyl-5,6-dihydro-7-ethyl-3-(2-thienyl)-9H-pyrazolo[3,4-c]-1,2,4-triazolo[4,3-a]pyridine
9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred LTD4-antagonists which may be mentioned include Montelukaste, Pranlukaste, Zafirlukaste, MCC-847 (ZD-3523), MN-001, MEN-91507 (LM-1507), VUF-5078, VUF-K-8707, L-733321 and
1-(((R)-(3-(2-(6,7-Difluoro-2-quinolinyl)ethenyl)phenyl)-3-(2-(2-hydroxy-2-propyl)phenyl)thio)methylcyclopropane-acetic acid,
1-(((1(R)-3(3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid
[2-[[2-(4-tert-Butyl-2-thiazolyl)-5-benzofuranyl]oxymethyl]phenyl]acetic acid optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

Examples of preferred EGFR-inhibitors which may be mentioned include Cetuximabe, Trastuzumabe, ABX-EGF, Mab ICR-62 and 4-[(3-Chlor-4-fluorphenyl)amino]-6-{[4-(morpholin-4-yl)-1-oxo-2-buten-1-yl]amino}-7-cyclopropylmethoxy-chinazoline 4-[(3-Chlor-4-fluorphenyl)amino]-6-{[4-(N,N-diethylamino)-1-oxo-2-buten-1-yl]amino}-7-cyclopropylmethoxy-chinazoline 4-[(3-Chlor-4-fluorphenyl)amino]-6-{[4-(N,N-dimethylamino)-1-oxo-2-buten-1-yl]amino}-7-cyclopropylmethoxy-chinazoline 4-[(R)-(1-Phenyl-ethyl)amino]-6-{[4-(morpholin-4-yl)-1-oxo-2-buten-1-yl]amino}-7-cyclopentyloxy-chinazoline 4-[(3-Chlor-4-fluor-phenyl)amino]-6-{[4-((R)-6-methyl-2-oxo-morpholin-4-yl)-1-oxo-2-buten-1-yl]amino}-7-cyclopropylmethoxy-chinazoline 4-[(3-Chlor-4-fluor-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-chinazoline 4-[(3-Chlor-4-fluor-phenyl)amino]-6-{[4-((R)-2-methoxymethyl-6-oxo-morpholin-4-yl)-1-oxo-2-buten-1-yl]amino}-7-cyclopropylmethoxy-chinazoline 4-[(3-Chlor-4-fluor-phenyl)amino]-6-[2-((S)-6-methyl-2-oxo-morpholin-4-yl)-ethoxy]-7-methoxy-chinazoline 4-[(3-Chlor-4-fluorphenyl)amino]-6-({4-[N-(2-methoxy-ethyl)-N-methyl-amino]-1-oxo-2-buten-1-yl}amino)-7-cyclopropylmethoxy-chinazoline 4-[(3-Chlor-4-fluorphenyl)amino]-6-{[4-(N,N-dimethylamino)-1-oxo-2-buten-1-yl]amino}-7-cyclopentyloxy-chinazoline 4-[(R)-(1-Phenyl-ethyl)amino]-6-{[4-(N,N-bis-(2-methoxy-ethyl)-amino)-1-oxo-2-buten-1-yl]amino}-7-cyclopropylmethoxy-chinazoline 4-[(R)-(1-Phenyl-ethyl)amino]-6-({4-[N-(2-methoxy-ethyl)-N-ethyl-amino]-1-oxo-2-buten-1-yl}amino)-7-cyclopropylmethoxy-chinazoline 4-[(R)-(1-Phenyl-ethyl)amino]-6-({4-[N-(2-methoxy-ethyl)-N-methyl-amino]-1-oxo-2-buten-1-yl}amino)-7-cyclopropylmethoxy-chinazoline 4-[(R)-(1-Phenyl-ethyl)amino]-6-({4-[N-(tetrahydropyran-4-yl)-N-methyl-amino]-1-oxo-2-buten-1-yl}amino)-7-cyclopropylmethoxy-chinazoline 4-[(3-Chlor-4-fluorphenyl)amino]-6-{[4-(N,N-dimethylamino)-1-oxo-2-buten-1-yl]amino}-7-((R)-tetrahydrofuran-3-yloxy)-chinazoline 4-[(3-Chlor-4-fluorphenyl)amino]-6-{[4-(N,N-dimethylamino)-1-oxo-2-buten-1-yl]amino}-7-((S)-tetrahydrofuran-3-yloxy)-chinazoline 4-[(3-Chlor-4-fluorphenyl)amino]-6-({4-[N-(2-methoxy-ethyl)-N-methyl-amino]-1-oxo-2-buten-1-yl}amino)-7-cyclopentyloxy-chinazoline 4-[(3-Chlor-4-fluorphenyl)amino]-6-{[4-(N-cyclopropyl-N-methyl-amino]-1-oxo-2-buten-1-yl]amino}-7-cyclopentyloxy-chinazoline 4-[(3-Chlor-4-fluorphenyl)amino]-6-{[4-(N,N-dimethylamino)-1-oxo-2-buten-1-yl]amino}-7-[(R)-(tetrahydrofuran-2-yl)methoxy]-chinazoline 4-[(3-Chlor-4-fluorphenyl)amino]-6-{[4-(N,N-dimethylamino)-1-oxo-2-buten-1-yl]amino}-7-[(S)-(tetrahydrofuran-2-yl)methoxy]-chinazoline 4-[(3-Ethinyl-phenyl)amino]-6,7-bis-(2-methoxy-ethoxy)-chinazoline 4-[(3-Chlor-4-fluorphenyl)amino]-7-[3-(morpholin-4-yl)-propyloxy]-6-[(vinylcarbonyl)amino]-chinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-buten-1-yl]amino}-7-ethoxy-chinoline 4-{[3-Chlor-4-(3-fluor-benzyloxy)-phenyl]amino}-6-(5-{[(2-methansulfonyl-ethyl)amino]methyl}-furan-2-yl)chinazoline 4-[(R)-(1-Phenyl-ethyl)amino]-6-{[4-((R)-6-methyl-2-oxo-morpholin-4-yl)-1-oxo-2-buten-1-yl]amino}-7-methoxy-chinazoline 4-[(3-Chlor-4-fluorphenyl)amino]-6-{[4-(morpholin-4-yl)-1-oxo-2-buten-1-yl]amino}-7-[(tetrahydrofuran-2-yl)methoxy]-chinazoline 4-[(3-Chlor-4-fluorphenyl)amino]-6-({4-[N,N-bis-(2-methoxy-ethyl)-amino]-1-oxo-2-buten-1-yl}amino)-7-[(tetrahydrofuran-2-yl)methoxy]-chinazoline 4-[(3-Ethinyl-phenyl)amino]-6-{[4-(5,5-dimethyl-2-oxo-morpholin-4-yl)-1-oxo-2-buten-1-yl]amino}-chinazoline 4-[(3-Chlor-4-fluor-phenyl)amino]-6-[2-(2,2-dimethyl-6-oxo-morpholin-4-yl)-ethoxy]-7-methoxy-chinazoline 4-[(3-Chlor-4-fluor-phenyl)amino]-6-[2-(2,2-dimethyl-6-oxo-morpholin-4-yl)-ethoxy]-7-[(R)-(tetrahydrofuran-2-yl)methoxy]-chinazoline 4-[(3-Chlor-4-fluor-phenyl)amino]-7-[2-(2,2-dimethyl-6-oxo-morpholin-4-yl)-ethoxy]-6-[(S)-(tetrahydrofuran-2-yl)methoxy]-chinazoline 4-[(3-Chlor-4-fluor-phenyl)amino]-6-{2-[4-(2-oxo-morpholin-4-yl)-pipendin-1-yl]-ethoxy}-7-methoxy-chinazoline 4-[(3-Chlor-4-fluor-phenyl)amino]-6-[1-(tert.-butyloxycarbonyl)-pipendin-4-yloxy]-7-methoxy-chinazoline 4-[(3-Chlor-4-fluor-phenyl)amino]-6-(trans-4-amino-cyclohexan-1-yloxy)-7-methoxy-chinazoline 4-[(3-Chlor-4-fluor-phenyl)amino]-6-(trans-4-methansulfonylamino-cyclohexan-1-yloxy)-7-methoxy-chinazoline 4-[(3-Chlor-4-fluor-phenyl)amino]-6-(tetrahydropyran-3-yloxy)-7-methoxy-chinazoline 4-[(3-Chlor-4-fluor-phenyl)amino]-6-(1-methyl-pipendin-4-yloxy)-7-methoxy-chinazoline 4-[(3-Chlor-4-fluor-phenyl)amino]-6-{1-[(morpholin-4-yl)carbonyl]-pipendin-4-yloxy}-7-methoxy-chinazoline 4-[(3-Chlor-4-fluor-phenyl)amino]-6-{1-[(methoxymethyl)carbonyl]-pipendin-4-yloxy}-7-methoxy-chinazoline 4-[(3-Chlor-4-fluor-phenyl)amino]-6-(pipendin-3-yloxy)-7-methoxy-chinazoline 4-[(3-Chlor-4-fluor-phenyl)amino]-6-[1-(2-acetylamino-ethyl)-pipendin-4-yloxy]-7-methoxy-chinazoline 4-[(3-Chlor-4-fluor-phenyl)amino]-6-(tetrahydropyran-4-yloxy)-7-ethoxy-chinazoline 4-[(3-Chlor-4-fluor-phenyl)amino]-6-((S)-tetrahydrofuran-3-yloxy)-7-hydroxy-chinazoline 4-[(3-Chlor-4-fluor-phenyl)amino]-6-(tetrahydropyran-4-yloxy)-7-(2-methoxy-ethoxy)-chinazoline 4-[(3-Chlor-4-fluor-phenyl)amino]-6-{trans-4-[(dimethylamino)sulfonylamino-cyclohexan-1-yloxy}-7-methoxy-chinazoline 4-[(3-Chlor-4-fluor-phenyl)amino]-6-{trans-4-[(morpholin-4-yl)carbonylamino]-cyclohexan-1-yloxy}-7-methoxy-chinazoline 4-[(3-Chlor-4-fluor-phenyl)amino]-6-{trans-4-[(morpholin-4-yl)sulfonylamino]-cyclohexan-1-yloxy}-7-methoxy-chinazoline 4-[(3-Chlor-4-fluor-phenyl)amino]-6-(tetrahydropyran-4-yloxy)-7-(2-acetylamino-ethoxy)-chinazoline 4-[(3-Chlor-4-fluor-phenyl)amino]-6-(tetrahydropyran-4-yloxy)-7-(2-methansulfonylamino-ethoxy)-chinazoline 4-[(3-Chlor-4-fluor-phenyl)amino]-6-{1-[(pipendin-1-yl)carbonyl]-pipendin-4-yloxy}-7-methoxy-chinazoline 4-[(3-Chlor-4-fluor-phenyl)amino]-6-(1-aminocarbonylmethyl-pipendin-4-yloxy)-7-methoxy-chinazoline 4-[(3-Chlor-4-fluor-phenyl)amino]-6-(cis-4-{N-[(tetrahydropyran-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)sulfonyl]-N-methyl-amino}-cyclohexan-1-yloxy)-7-methoxy-chinazoline 4-[(3-Chlor-4-fluor-phenyl)amino]-6-(trans-4-ethansulfonylamino-cyclohexan-1-yloxy)-7-methoxy-chinazoline 4-[(3-Chlor-4-fluor-phenyl)amino]-6-(1-methansulfonyl-pipendin-4-yloxy)-7-ethoxy-chinazoline 4-[(3-Chlor-4-fluor-phenyl)amino]-6-(1-methansulfonyl-pipendin-4-yloxy)-7-(2-methoxy-ethoxy)-chinazoline 4-[(3-Chlor-4-fluor-phenyl)amino]-6-[1-(2-methoxy-acetyl)-pipendin-4-yloxy]-7-(2-methoxy-ethoxy)-chinazoline 4-[(3-Chlor-4-fluor-phenyl)amino]-6-(cis-4-acetylamino-cyclohexan-1-yloxy)-7-methoxy-chinazoline 4-[(3-Ethinyl-phenyl)amino]-6-[1-(tert-butyloxycarbonyl)-pipendin-4-yloxy]-7-methoxy-chinazoline 4-[(3-Ethinyl-phenyl)amino]-6-(tetrahydropyran-4-yloxy)-7-methoxy-chinazoline 4-[(3-Chlor-4-fluor-phenyl)amino]-6-(cis-4-{N-[(piperidin-1-yl)carbonyl]-N-methyl-amino}-cyclohexan-1-yloxy)-7-methoxy-chinazoline 4-[(3-Chlor-4-fluor-phenyl)amino]-6-(cis-4-{N-[(4-methyl-piperazin-1-yl)carbonyl]-N-methyl-amino}-cyclohexan-1-yloxy)-7-methoxy-chinazoline 4-[(3-Chlor-4-fluor-phenyl)amino]-6-{cis-4-[(morpholin-4-yl)carbonylamino]-cyclohexan-1-yloxy}-7-methoxy-chinazoline 4-[(3-Chlor-4-fluor-phenyl)amino]-6-{1-[2-(2-oxopyrrolidin-1-yl)ethyl]-pipendin-4-yloxy}-7-methoxy-chinazoline 4-[(3-Chlor-4-fluor-phenyl)amino]-6-{1-[(morpholin-4-yl)carbonyl]-piperidin-4-yloxy}-7-(2-methoxy-ethoxy)-chinazoline 4-[(3-Ethinyl-phenyl)amino]-6-(1-acetyl-pipendin-4-yloxy)-7-methoxy-chinazoline 4-[(3-Ethinyl-phenyl)amino]-6-(1-methyl-pipendin-4-yloxy)-7-methoxy-chinazoline 4-[(3-Ethinyl-phenyl)amino]-6-(1-methansulfonyl-pipendin-4-yloxy)-7-methoxy-chinazoline 4-[(3-Chlor-4-fluor-phenyl)amino]-6-(1-methyl-pipendin-4-yloxy)-7-(2-methoxy-ethoxy)-chinazoline 4-[(3-Chlor-4-fluor-phenyl)amino]-6-(1-isopropyloxycarbonyl-pipendin-4-yloxy)-7-methoxy-chinazoline 4-[(3-Chlor-4-fluor-phenyl)amino]-6-(cis-4-methylamino-cyclohexan-1-yloxy)-7-methoxy-chinazoline 4-[(3-Chlor-4-fluor-phenyl)amino]-6-{cis-4-[N-(2-methoxy-acetyl)-N-methyl-amino-cyclohexan-1-yloxy}-7-methoxy-chinazoline 4-[(3-Ethinyl-phenyl)amino]-6-(pipendin-4-yloxy)-7-methoxy-chinazoline 4-[(3-Ethinyl-phenyl)amino]-6-[1-(2-methoxy-acetyl)-pipendin-4-yloxy]-7-methoxy-chinazoline 4-[(3-Ethinyl-phenyl)amino]-6-{1-[(morpholin-4-yl)carbonyl]-pipendin-4-yloxy}-7-methoxy-chinazoline 4-[(3-Chlor-4-fluor-phenyl)amino]-6-{1-[(cis-2,6-dimethyl-morpholin-4-yl)carbonyl]-pipendin-4-yloxy}-7-methoxy-chinazoline 4-[(3-Chlor-4-fluor-phenyl)amino]-6-{1-[(2-methyl-morpholin-4-yl)carbonyl]-pipendin-4-yloxy}-7-methoxy-chinazoline 4-[(3-Chlor-4-fluor-phenyl)amino]-6-{1-[(S,S)-(2-oxa-5-aza-bicyclo[2.2.1]hept-5-yl)carbonyl]-pipendin-4-yloxy}-7-methoxy-chinazoline 4-[(3-Chlor-4-fluor-phenyl)amino]-6-{1-[(N-methyl-N-2-methoxyethyl-amino)carbonyl]-pipendin-4-yloxy}-7-methoxy-chinazoline 4-[(3-Chlor-4-fluor-phenyl)amino]-6-(1-ethyl-pipendin-4-yloxy)-7-methoxy-chinazoline 4-[(3-Chlor-4-fluor-phenyl)amino]-6-{1-[(2-methoxyethyl)carbonyl]-pipendin-4-yloxy}-7-methoxy-chinazoline 4-[(3-Chlor-4-fluor-phenyl)amino]-6-{1-[(3-methoxypropyl-amino)-carbonyl]-pipendin-4-yloxy}-7-methoxy-chinazoline 4-[(3-Chlor-4-fluor-phenyl)amino]-6-[cis-4-(N-methansulfonyl-N-methyl-amino)-cyclohexan-1-yloxy]-7-methoxy-chinazoline 4-[(3-Chlor-4-fluor-phenyl)amino]-6-[cis-4-(N-acetyl-N-methyl-amino)-cyclohexan-1-yloxy]-7-methoxy-chinazoline 4-[(3-Chlor-4-fluor-phenyl)amino]-6-(trans-4-methylamino-cyclohexan-1-yloxy)-7-methoxy-chinazoline 4-[(3-Chlor-4-fluor-phenyl)amino]-6-[trans-4-(N-methansulfonyl-N-methyl-amino)-cyclohexan-1-yloxy]-7-methoxy-chinazoline 4-[(3-Chlor-4-fluor-phenyl)amino]-6-(trans-4-dimethylamino-cyclohexan-1-yloxy)-7-methoxy-chinazoline 4-[(3-Chlor-4-fluor-phenyl)amino]-6-(trans-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-[2-(2,2-dimethyl-6-oxo-morpholin-4-yl)-ethoxy]-7-[(S)-(tetrahydrofuran-2-yl)methoxy]-chinazoline 4-[(3-Chlor-4-fluor-phenyl)amino]-6-(1-methansulfonyl-pipendin-4-yloxy)-7-methoxy-chinazoline 4-[(3-Chlor-4-fluor-phenyl)amino]-6-(1-cyano-piperidin-4-yloxy)-7-methoxy-chinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred dopamin antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Desloratidine and Meclozine, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred PAF antagonists which may be mentioned include
4-(2-Chlorphenyl)-9-methyl-2-[3(4-morpholinyl)-3-propanon-1-yl]-6H-thieno-[3,2-f]-[1,2,4]triazolo[4,3-a][1,4]diazepine
6-(2-Chlorphenyl)-8,9-dihydro-1-methyl-8-[(4-morpholinyl)carbonyl]-4H,7H-cyclo-penta-[4,5]thieno-[3,2f][1,2,4]triazolo[4,3-a][1,4]diazepine
optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred MRP4-Inhibitors which may be mentioned include N-Acetyl-dinitrophenyl-Cysteine, cGMP, Cholate, Diclofenac, Dehydroepiandrosterone 3-glucuronide, Dehydroepiandrosterone 3-sulphate, Dilazep, Dinitrophenyl-5-glutathione, Estradiol 17-β-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycolithocholic acid sulphate, Ibuprofen, Indomethacin, Indoprofen, Ketoprofen, Lithocholic acid sulphate, Methotrexate, MK571 ((E)-3-[[[3-[2-(7-Chloro-2-quinolinyl)ethenyl]phenyl]-[[3-dimethylamino)-3-oxopropyl]thio]methyl]thio]-propanoic acid), α-Naphthyl-β-D-glucuronide, Nitrobenzyl mercaptopurine riboside, Probenecid, PSC833, Sildenafil, Sulfinpyrazone, Taurochenodeoxycholate, Taurocholate, Taurodeoxycholate, Taurolithocholate, Taurolithocholic acid sulphate, Topotecan, Trequinsin, Zaprinast and Dipyridamol, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Especially preferred are N-Acetyl-dinitrophenyl-Cysteine, Dehydroepiandrosterone 3-sulphate, Dilazep, Dinitrophenyl-5-glutathione, Estradiol 3,17-disulphate, Flurbiprofen, Glycocholate, Glycolithocholic acid sulphate, Ibuprofen, Indomethacin, Indoprofen, Lithocholic acid sulphate, MK571, PSC833, Sildenafil, Taurochenodeoxycholate, Taurocholate, Taurolithocholate, Taurolithocholic acid sulphate, Trequinsin, Zaprinast and Dipyridamol, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydronitrate, hydrofumarate, hydrotartrate, hydrooxalate, hydrosuccinate, hydrobenzoate and hydro-p-toluenesulfonate.

Examples of preferred iNOS-Inhibitors which may be mentioned include S-(2-Aminoethyl)isothio-urea, Aminoguanidin, 2-Aminomethylpyridin, AMT, L-Canavanin, 2-Iminopiperidin, S-Isopropylisothioharnstoff, S-Methylisothio-urea, S-Ethylisothioharnstoff, S-Methyltiocitrullin, S-Ethylthiocitrullin, L-NA ($N^\omega$-Nitro-L-arginin), L-NAME ($N^\omega$-Nitro-L-argininmethylester), L-NMMA ($N^\omega$-Monomethyl-L-arginin), L-N10 ($N^{107}$-Iminoethyl-L-ornithin), L-NIL ($N^\omega$-Iminoethyl-lysin), (S)-6-Acetimidoylamino-2-amino-hexanoic acid (1H-tetrazol-5-yl)-amid (SC-51), 1400W, (S)-4-(2-Acetimidoylamino-ethylsulfanyl)-2-amino-buturic acid (GW274150), 2-[2-(4-Methoxy-pyridin-2-yl)-ethyl]-3H-imidazo[4,5-b]pyridin (BYK191023), 2-((R)-3-Amino-1-phenyl-propoxy)-4-chlor-5-fluorbenzonitril, 2-((1R,3S)-3-Amino-4-hydroxy-1-thiazol-5-yl-butylsulfanyl)-6-trifluoromethyl-nicotinonitril, 2-((1R,3S)-3-Amino-4-hydroxy-1-thiazol-5-yl-butylsulfanyl)-4-chlor-benzonitril, 2-((1R,3S)-3-Amino-4-hydroxy-1-thiazol-5-yl-butylsulfanyl)-5-chlor-benzonitril, (2S,4R)-2-Amino-4-(2-chlor-5-trifluoromethyl-phenylsulfanyl)-4-thiazol-5-yl-butan-1-ol, 2-((1R,3S)-3-Amino-4-hydroxy-1-thiazol-5-yl-butylsulfanyl)-5-chlor-nicotinonitril, 4-((S)-3-Amino-4-hydroxy-1-phenyl-butylsulfanyl)-6-methoxy-nicotinonitril, substituierte 3-Phenyl-3,4-dihydro-1-isoquinolinamin wie z.B. AR-C102222, (1S,5S,6R)-7-Chlor-5-methyl-2-aza-bicyclo[4.1.0]hept-2-en-3-ylamin (ONO-1714), (4R,5R)-5-Ethyl-4-methyl-thiazolidin-2-ylideneamin, (4R,5R)-5-Ethyl-4-methyl-selenazolidin-2-ylideneamin, 4-Aminotetrahydro-biopterin, (E)-3-(4-Chlor-phenyl)-N-(1-{2-oxo-2-[4-(6-trifluormethyl-pyrimidin-4-yloxy)-piperidin-1-yl]-ethylcarbamoyl}-2-pyridin-2-yl-ethyl)-acrylamid (FR260330), 3-(2,4-Difluor-phenyl)-6-[2-(4-imidazol-1-yl-methyl-phenoxy)-ethoxy]-2-phenyl-pyridin (PPA250), 3-{[(Benzo[1,3]dioxol-5-ylmethyl)-carbamoyl]-methyl}-4-(2-imidazol-1-yl-pyrimidin-4-yl)-piperazin-1-carbonsäuremethylester (BBS-1), (R)-1-(2-Imidazol-1-yl-6-methyl-pyrimidin-4-yl)-pyrrolidin-2-carbonsäure (2-benzo[1,3]dioxol-5-yl-ethyl)amid (BBS-2), optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Further examples of preferred iNOS-Inhibitors which may be mentioned include antisense-Oligonucleotide, especially those antisense-Oligonucleotide bindung iNOS-coding nucleinic acids, examples therefore are disclosed in WO 01/52902.

Examples of preferred SYK-inhibitors which may be mentioned include
2-[(2-aminoethyl)amino]-4-[(3-bromophenyl)amino]-5-Pyrimidinecarboxamide;
2-[[7-(3,4-dimethoxyphenyl)imidazo[1,2-c]pyrimidin-5-yl]amino]-3-Pyridinecarboxamide;
6-[[5-fluoro-2-[3,4,5-trimethoxyphenyl)amino]-4-pyrimidinyl]amino]-2,2-dimethyl-2H-Pyrido[3,2-b]-1,4-oxazin-3 (4H)-one;
N-[3-bromo-7-(4-methoxyphenyl)-1,6-naphthyridin-5-yl]-1,3-Propanediamin 7-(4-methoxyphenyl)-N-methyl-1,6-Naphthyridin-5-amine;
N-[7-(4-methoxyphenyl)-1,6-naphthyridin-5-yl]-1,3-Propanediamine;
N-[7-(2-thienyl)-1,6-naphthyridin-5-yl-1,3-Propanediamine;
N-[7-(4-(dimethylamino)phenyl]-1,6-naphthyridin-5-yl]-1,2-Ethanediamine;
N-[7-(4-methoxyphenyl)-2-(trifluoromethyl)-1,6-naphthyridin-5-yl]-1,3-Propanediamine;
N-[7-(4-methoxyphenyl)-3-phenyl-1,6-naphthyridin-5-yl]-1,3-Propanediamine;
N-(7-phenyl-1,6-naphthyridin-5-yl)-1,3-Propanediamine;
N-[7-(3-fluorophenyl)-1,6-naphthyridin-5-yl]-1,3-Propanediamine;
N-[7-(3-chlorophenyl)-1,6-naphthyridin-5-yl]-1,3-Propanediamine;
N-[7-[3-(trifluoromethoxy)phenyl]-1,6-naphthyridin-5-yl]-1,3-Propanediamine;
N-[7-(4-fluorophenyl)-1,6-naphthyridin-5-yl]-1,3-Propanediamine;
N-[7-(4-fluorophenyl)-1,6-naphthyridin-5-yl]-1,3-Propanediamine;
N-[7-(4-chlorophenyl)-1,6-naphthyridin-5-yl]-1,3-Propanediamine;
N-[7-(4'-methyl[1,1'-biphenyl]-4-yl)-1,6-naphthyridin-1,3-Propanediamine;
N-[7-[4-(dimethylamino)phenyl]-1,6-naphthyridin-5-yl]-1,3-Propanediamine;
N-[7-[4-(diethylamino)phenyl]-1,6-naphthyridin-5-yl]-1,3-Propanediamine;
N-[7-[4-(4-morpholinyl)phenyl]-1,6-naphthyridin-5-yl]-1,3-Propanediamine;
N-[7-[4-[[2-(dimethylamino)ethyl]methylamino]phenyl]-1,6-naphthyridin-5-yl]-1,3-Propanediamine;
N-[7-(4-bromophenyl)-1,6-naphthyridin-5-yl]-1,3-Propanediamine;
N-[7-(4-methylphenyl)-1,6-naphthyridin-5-yl]-1,3-Propanediamine;
N-[7-[4-(methylthio)phenyl]-1,6-naphthyridin-5-yl]-1,3-Propanediamine;
N-[7-[4-(1-methylethyl)phenyl]-1,6-naphthyridin-5-yl]-1,3-Propanediamine;
7-[4-(dimethylamino)phenyl]-N-methyl-1,6-Naphthyridin-5-amine;
7-[4-(dimethylamino)phenyl]-N,N-dimethyl-1,6-Naphthyridin-5-amine;
N-[7-[4-(dimethylamino)phenyl]-1,6-naphthyridin-5-yl]-1,4-Butanediamine;
N-[7-[4-(dimethylamino)phenyl]-1,6-naphthyridin-5-yl]-1,5-Pentanediamine;
3-[[7-[4-(dimethylamino)phenyl]-1,6-naphthyridin-5-yl]oxy]-1-Propanole;
4-[5-(4-aminobutoxy)-1,6-naphthyridin-7-yl]-N,N-dimethyl-Benzenamine;
4-[[7-[4-(dimethylamino)phenyl]-1,6-naphthyridin-5-yl]amino]-1-Butanole;
N-[7-[4-(dimethylamino)phenyl]-1,6-naphthyridin-5-yl]-N-methyl-1,3-Propanediamine;
N-[7-[4-(dimethylamino)phenyl]-1,6-naphthyridin-5-yl]N'-methyl-1,3-Propanediamine;
N-[7-[4-(dimethylamino)phenyl]-1,6-naphthyridin-5-yl]-N,N'-dimethyl-1,3-Propanediamine;
1-amino-3-[[7-[4-(dimethylamino)phenyl]-1,6-naphthyridin-5-yl]amino]-2-Propanole;
N-[7-[4-(dimethylamino)phenyl]-1,6-naphthyridin-5-yl]-2,2-dimethyl-1,3-Propanediamine;
7-[4-(dimethylamino)phenyl]-N-(3-pyridinylmethyl)-1,6-Naphthyridin-5-amine;
N-[(2-aminophenyl)methyl]-7-[4-(dimethylamino)phenyl]-1,6-Naphthyridin-5-amine;
N-[7-[6-(dimethylamino)[1,1'-biphenyl]-3-yl]-1,6-naphthyridin-5-yl]-1,3-Propanediamine;
N-[7-[3-chloro-4-(diethylamino)phenyl]-1,6-naphthyridin-5-yl]-1,3-Propanediamine;
N-[7-[4-(dimethylamino)-3-methoxyphenyl]-1,6-naphthyridin-5-yl]-1,3-Propanediamine;
N-[7-[4-(diethylamino)phenyl]-3-methyl-1,6-naphthyridin-5-yl]-1,3-Propanediamine;
N-[7-(3'-fluoro[1,1'-biphenyl]-3-yl)-1,6-naphthyridin-5-yl]-1,2-Ethanediamin,
N-[7-(4-methoxyphenyl)-1,6-naphthyridin-5-yl]-1,6-Naphthyridine-1,3-Propanediamine;
N,N'-bis(3-aminopropyl)-7-(4-methoxyphenyl)-2,5-diamine;
N-[7-(4-methoxyphenyl)-2-(phenylmethoxy)-1,6-naphthyridin-5-yl]-1,6-Naphthyridine-1,3-Propanediamine;
N5-(3-aminopropyl)-7-(4-methoxyphenyl)-N2-(phenylmethyl)-2,5-diamine;
N-[7-(2-naphthalenyl)-1,6-naphthyridin-5-yl]-1,3-Propanediamine;
N-[7-(2'-fluoro[1,1'-biphenyl]-4-yl)-1,6-naphthyridin-5-yl]-1,3-Propanediamine;
N-[7-(3,4,5-trimethoxyphenyl)-1,6-naphthyridin-5-yl]-1,3-Propanediamine;
N-[7-(3,4-dimethylphenyl)-1,6-naphthyridin-5-yl]-1,3-Propanediamine;
1-amino-3-[[7-(2-naphthalenyl)-1,6-naphthyridin-5-yl]amino]-2-Propanole;
1-amino-3-[[7-(2'-fluoro[1,1'-biphenyl]-4-yl)-1,6-naphthyridin-5-yl]amino]-2-Propanole;
1-amino-3-[[7-(4'-methoxy[1,1'-biphenyl]-4-yl)-1,6-naphthyridin-5-yl]amino]-2-Propanole;
1-amino-3-[[7-(3,4,5-trimethoxyphenyl)-1,6-naphthyridin-5-yl]amino]-2-Propanole;
1-amino-3-[[7-(4-bromophenyl)-1,6-naphthyridin-5-yl]amino]-2-Propanole;
N-[7-(4'-methoxy[1,1'-biphenyl]-4-yl)-1,6-naphthyridin-5-yl]-2,2-dimethyl-1,3-Propanediamine;
1-[[7-[4-(dimethylamino)phenyl]-1,6-naphthyridin-5-yl]amino]-2-Propanole;
2-[[2-[[7-[4-(dimethylamino)phenyl]-1,6-naphthyridin-5-yl]amino]ethyl]thio]-Ethanole;
7-[4-(dimethylamino)phenyl]-N-(3-methyl-5-isoxazolyl)-1,6-Naphthyridin-5-amine;
7-[4-(dimethylamino)phenyl]-N-4-pyrimidinyl-1,6-Naphthyridin-5-amine;
N-[7-[4-(dimethylamino)phenyl]-1,6-naphthyridin-5-yl]-1,3-Cyclohexanediamine;
N,N-dimethyl-4-[5-(1-piperazinyl)-1,6-naphthyridin-7-yl]-Benzenamine;
4-[5-(2-methoxyethoxy)-1,6-naphthyridin-7-yl]-N,N-dimethyl-Benzenamine;
1-[7-[4-(dimethylamino)phenyl]-1,6-naphthyridin-5-yl]-4-Piperidinole;
1-[7-[4-(dimethylamino)phenyl]-1,6-naphthyridin-5-yl]-3-Pyrrolidinole;
7-[4-(dimethylamino)phenyl]-N-(2-furanylmethyl)-1,6-Naphthyridin-5-amine;
7-[4-(dimethylamino)phenyl]-N-[3-(1H-imidazol-1-yl)propyl]-1,6-Naphthyridin-5-amine;
1-[7-[4-(dimethylamino)phenyl]-1,6-naphthyridin-5-yl]-4-Piperidinecarboxamide;

1-[3-[[7-[4-(dimethylamino)phenyl]-1,6-naphthyridin-5-yl]amino]propyl]-2-Pyrrolidinone;
N-[3'-[5-[(3-aminopropyl)amino]-1,6-naphthyridin-7-yl][1,1'-biphenyl]-3-yl]-Acetamide;
N-[7-(4'-fluoro[1,1'-biphenyl]-4-yl)-1,6-naphthyridin-5-yl]-1,3-Propanediamine;
N-[4'-[5-[(3-aminopropyl)amino]-1,6-naphthyridin-7-yl][1,1'-biphenyl]-3-yl]-Acetamide;
N-[7-[4-(1,3-benzodioxol-5-yl)phenyl]-1,6-naphthyridin-5-yl]-1,3-Propanediamine;
N-[7-[4-(2-thienyl)phenyl]-1,6-naphthyridin-5-yl]-1,3-Propanediamine;
N-[7-[4-fluoro-3-(trifluoromethyl)phenyl]-1,6-naphthyridin-5-yl]-1,3-Propanediamine;
N-[7-[4-(3-pyridinyl)phenyl]-1,6-naphthyridin-5-yl]-1,3-Propanediamine;
N-[7-(1,3-benzodioxol-5-yl)-1,6-naphthyridin-5-yl]-1,3-Propanediamine;
N-[7-(6-methoxy-2-naphthalenyl)-1,6-naphthyridin-5-yl]-1,3-Propanediamine;
7-[4-(dimethylamino)phenyl]-N-(4-pyridinylmethyl)-1,6-Naphthyridin-5-amine;
3-[[7-[4-(dimethylamino)phenyl]-1,6-naphthyridin-5-yl]methylamino]-Propanenitrile;
7-[4-(dimethylamino)phenyl]-N-[1-(phenylmethyl)-4-piperidinyl]-1,6-Naphthyridin-5-amine;
N-[7-[4-(dimethylamino)phenyl]-1,6-naphthyridin-5-yl]-1,2-Cyclohexanediamin, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Pharmaceutical Forms

The compounds of formula 1 are administered to a mammal in a therapeutically effective amount. By "therapeutically effective amount" it is meant an amount of a compound of formula 1 that, when administered alone or in combination with an additional therapeutic agent to a mammal, is effective to prevent or ameliorate diseases, wherein the activity of a CCR-3-receptor is involved, or the progression of this disease.

Suitable preparations for administering the compounds of formula 1 include for example tablets, capsules, suppositories, solutions and powders etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

For administering the compounds of formula 1 it is particularly preferred according to the invention to use preparations or pharmaceutical formulations which are suitable for inhalation. Inhalable preparations include inhalable powders, propellant-containing metered-dose aerosols or propellant-free inhalable solutions. Within the scope of the present invention, the term propellant-free inhalable solutions also includes concentrates or sterile inhalable solutions ready for use. The formulations which may be used within the scope of the present invention are described in more detail in the next part of the specification.

The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred. Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the μg range. The dosage may then be in the gram range, for example.

In another aspect the present invention relates to the above-mentioned pharmaceutical formulations as such which are characterised in that they contain a compound of formula 1, particularly the above-mentioned pharmaceutical formulations which can be administered by inhalation.

The following examples of formulations illustrate the present invention without restricting its scope:

Examples of Pharmaceutical Formulations

| A) | Tablets | per tablet |
|---|---|---|
| | active substance 1 | 100 mg |
| | lactose | 140 mg |
| | maize starch | 240 mg |
| | polyvinylpyrrolidone | 15 mg |
| | magnesium stearate | 5 mg |
| | | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) | Tablets | per tablet |
|---|---|---|
| | active substance 1 | 80 mg |
| | lactose | 55 mg |
| | maize starch | 190 mg |
| | microcrystalline cellulose | 35 mg |
| | polyvinylpyrrolidone | 15 mg |
| | sodium carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance 1 | 50 mg |
| | sodium chloride | 50 mg |
| | water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

| D) | Metering aerosol | |
|---|---|---|
| | active substance 1 | 0.005 |
| | sorbitan trioleate | 0.1 |
| | monofluorotrichloromethane and TG134a:TG227 2:1 | ad 100 |

The suspension is transferred into a conventional aerosol container with metering valve. Preferably 50 μl suspension are released on each actuation. The active substance may also be released in higher doses if desired (e.g. 0.02 wt.-%).

| E) | Solutions (in mg/100 ml) | |
|---|---|---|
| | active substance 1 | 333.3 mg |
| | benzalkonium chloride | 10.0 mg |
| | EDTA | 50.0 mg |
| | HCl (1N) | ad pH 3.4 |

This solution can be prepared in the usual way.

| F) | Inhalable powder | |
|---|---|---|
| | active substance 1 | 12 μg |
| | lactose monohydrate | ad 25 mg |

The inhalable powder is prepared in the usual way by mixing the individual ingredients.

What we claim:

1. A compound of formula 1

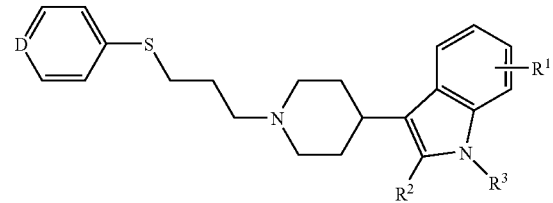

$R^1$ is H, halogen or $OR^{1.1}$;
$R^{1.1}$ H or $C_{1-6}$-alkyl
$R^2$ is $C_{1-6}$-alkyl, $C_{3-8}$-cycloalkyl, $C(R^{2.1})_2OR^{2.1}$ or $C(R^{2.1})_2N(R^{2.1})_2$;
$R^{2.1}$ H, $C_{1-6}$-alkyl or $C_{3-8}$-cycloalkyl;
$R^3$ is a group A optionally substituted by one or more $R^{3.1}$;
A is $C_{3-8}$-cycloalkyl, het or an annelated species of aryl or het;
$R^{3.1}$ is $C_{1-6}$-alkyl, $COOR^{3.1.2}$, $C_{1-6}$-alkyl-$COOR^{3.1.2}$, $C_{1-6}$-alkyl-COO—$C_{1-6}$-alkyl-$R^{3.1.1}$, $CH_2R^{3.1.1}$, $NHCOR^{3.1.3}$, $CON(R^{3.1.3})_2$, $C_{1-6}$-alkyl-CON $(R^{3.1.3})_2$, COO—$C_{1-6}$-alkyl-$R^{3.1.1}$, $N(R^{3.1.2})_2$, $OR^{3.1.2}$, $NO_2$, $SO_2N(R^{3.1.2})_2$;
$R^{3.1.1}$ is $NHC_{1-6}$-alkyl, $N(C_{1-6}$-alkyl$)_2$, an aromatic or nonaromatic 5 or 6 membered heterocycle containing one or two atoms selected from the group consisting of nitrogen, oxygen and sulfur, optionally substituted with a carbonyl group;
$R^{3.1.2}$ is H or $C_{1-6}$-alkyl;
$R^{3.1.3}$ is H, $C_{1-6}$-alkyl or $C_{3-8}$-cycloalkyl, optionally substituted with halogen, $COOR^{3.1.3.1}$, $COR^{3.1.3.1}$, $CONR^{3.1.3.1}R^{3.1.3.2}$, $NR^{3.1.3.1}R^{3.1.3.2}$, $NR^{3.1.3.1}SO_2R^{3.1.3.2}$, $OR^{3.1.3.1}$, $SR^{3.1.3.1}$, $SOR^{3.1.3.1}$, $SO_2R^{3.1.3.1}$ or $SO_2NR^{3.1.3.1}R^{3.1.3.2}$;

$R^{3.1.3.1}$ is H, $C_{1-6}$-alkyl or $C_{3-8}$-cycloalkyl;

$R^{3.1.3.2}$ is H, $C_{1-6}$-alkyl or $C_{3-8}$-cycloalkyl;

D is $CR^4$ or N $R^4$ is F or H;

and pharmaceutically acceptable salts thereof.

2. A compound of formula 1 according to claim 1, wherein
$R^1$ is H or halogen;
$R^2$ is $C_{1-6}$-alkyl or $C_{3-8}$-cycloalkyl;
$R^3$ is a group A optionally substituted by one or more $R^{3.1}$;
  A is $C_{3-8}$-cycloalkyl, an aromatic or nonaromatic 5 or 6 membered heterocycle containing one or two atoms selected from the group consisting of nitrogen, oxygen and sulfur or an annelated species of aryl or het;
  $R^{3.1}$ is $C_{1-6}$-alkyl, $COOR^{3.1.2}$, $C_{1-6}$-alkyl-$COOR^{3.1.2}$, $C_{1-6}$-alkyl-COO—$C_{1-6}$-alkyl-$R^{3.1.1}$, $CH_2R^{3.1.1}$, $NHCOR^{3.1.3}$, $CON(R^{3.1.3})_2$, $C_{1-6}$-alkyl-CON$(R^{3.1.3})_2$, COO—$C_{1-6}$-alkyl-$R^{3.1.1}$, $N(R^{3.1.2})_2$, $OR^{3.1.2}$, $NO_2$, $SO_2N(R^{3.1.2})_2$;
  $R^{3.1.1}$ is $NHC_{1-6}$-alkyl, $N(C_{1-6}$-alkyl$)_2$, an aromatic or nonaromatic 5 or 6 membered heterocycle containing one or two atoms selected from the group consisting of nitrogen, oxygen and sulfur, optionally substituted with a carbonyl group;
  $R^{3.1.2}$ is H or $C_{1-6}$-alkyl;
  $R^{3.1.3}$ is H, $C_{1-6}$-alkyl or $C_{3-8}$-cycloalkyl, optionally substituted with halogen, $COOR^{3.1.3.1}$, $COR^{3.1.3.1}$, $CONR^{3.1.3.1}R^{3.1.3.2}$, $NR^{3.1.3.1}R^{3.1.3.2}$, $NR^{3.1.3.1}SO_2R^{3.1.3.2}$, $OR^{3.1.3.1}$, $SR^{3.1.3.1}$, $SOR^{3.1.3.1}$, $SO_2R^{3.1.3.1}$ or $SO_2NR^{3.1.3.1}R^{3.1.3.2}$;
  $R^{3.1.3.1}$ is H, $C_{1-6}$-alkyl or $C_{3-8}$-cycloalkyl;
  $R^{3.1.3.2}$ is H, $C_{1-6}$-alkyl or $C_{3-8}$-cycloalkyl;

D is $CR^4$ or N $R^4$ is F or H;

and pharmaceutically acceptable salts thereof.

3. A compound of formula 1 according to claim 1, wherein
$R^1$ is H or halogen;
$R^2$ is $C_{1-6}$-alkyl or $C_{3-8}$-cycloalkyl;
$R^3$ is a group A optionally substituted by one or more $R^{3.1}$;
  A is $C_{3-8}$-cycloalkyl, an aromatic or nonaromatic 5 or 6 membered heterocycle containing one or two atoms selected from the group consisting of nitrogen, oxygen and sulfur or an annelated species of aryl or het;
  $R^{3.1}$ is $NHCOR^{3.1.3}$, $CON(R^{3.1.3})_2$, $C_{1-6}$-alkyl-CON$(R^{3.1.3})_2$;
  $R^{3.1.3}$ is H, $C_{1-6}$-alkyl or $C_{3-8}$-cycloalkyl, optionally substituted with halogen, $COOR^{3.1.3.1}$, $COR^{3.1.3.1}$, $CONR^{3.1.3.1}R^{3.1.3.2}$, $NR^{3.1.3.1}R^{3.1.3.2}$, $NR^{3.1.3.1}SO_2R^{3.1.3.2}$, $OR^{3.1.3.1}$, $SR^{3.1.3.1}$, $SOR^{3.1.3.1}$, $SO_2R^{3.1.3.1}$ or $SO_2NR^{3.1.3.1}R^{3.1.3.2}$;
  $R^{3.1.3.1}$ is H, $C_{1-6}$-alkyl or $C_{3-8}$-cycloalkyl;
  $R^{3.1.3.2}$ is H, $C_{1-6}$-alkyl or $C_{3-8}$-cycloalkyl;

D is $CR^4$ or N $R^4$ is F or H;

and pharmaceutically acceptable salts thereof.

4. A compound of formula 1 according to claim 1, wherein
$R^1$ is H or halogen;
$R^2$ is $C_{1-6}$-alkyl, $C_{3-8}$-cycloalkyl;
$R^3$ is a group A optionally substituted by one or more $R^{3.1}$;
  A is $C_{3-8}$-cycloalkyl, an aromatic or nonaromatic 5 or 6 membered heterocycle containing one or two atoms selected from the group consisting of nitrogen, oxygen and sulfur or an annelated species of aryl or het;
  $R^{3.1}$ is $C_{1-6}$-alkyl, $COOR^{3.1.2}$, $C_{1-6}$-alkyl-$COOR^{3.1.2}$, $C_{1-6}$-alkyl-COO—$C_{1-6}$-alkyl-$R^{3.1.1}$, $CH_2R^{3.1.1}$, COO—$C_{1-6}$-alkyl-$R^{3.1.1}$, $N(R^{3.1.2})_2$, $OR^{3.1.2}$, $NO_2$, $SO_2N(R^{3.1.2})_2$;
  $R^{3.1.1}$ is $NHC_{1-6}$-alkyl, $N(C_{1-6}$-alkyl$)_2$, an aromatic or nonaromatic 5 or 6 membered heterocycle containing one or two atoms selected from the group consisting of nitrogen, oxygen and sulfur, optionally substituted with a carbonyl group;
  $R^{3.1.2}$ is H or $C_{1-6}$-alkyl;

D is $CR^4$ or N $R^4$ is F or H;

and pharmaceutically acceptable salts thereof.

5. A compound of formula 1 according to claim 1, wherein
$R^1$ is H or halogen;
$R^2$ is $C_{1-6}$-alkyl or $CH_2O$—$C_{1-6}$-alkyl;
$R^3$ is a group A optionally substituted by one or more $R^{3.1}$;
  A is $C_{3-8}$-cycloalkyl or an aromatic or nonaromatic 5 or 6 membered heterocycle containing one or two nitrogen atoms;
  $R^{3.1}$ is $C_{1-6}$-alkyl, $COOR^{3.1.2}$, $C_{1-6}$-alkyl-$COOR^{3.1.2}$, $CH_2R^{3.1.1}$, CONH—$C_{1-6}$-alkyl-$R^{3.1.1}$, COO—$C_{1-6}$-alkyl-$R^{3.1.1}$, OH, O—$C_{1-6}$-alkyl, $NO_2$, $SO_2N(R^{3.1.2})_2$;
  $R^{3.1.1}$ is $NHC_{1-6}$-alkyl, $N(C_{1-6}$-alkyl$)_2$, an aromatic or nonaromatic 5 or 6 membered heterocycle containing one or two nitrogen atoms optionally substituted with a carbonyl group;
  $R^{3.1.2}$ is H or $C_{1-6}$-alkyl;
$R^{3.2}$ is H or $C_{1-6}$-alkyl;

D is $CR^4$ or N $R^4$ is F;

and pharmaceutically acceptable salts thereof.

6. A compound of formula 1 according to claim 1, wherein
$R^1$ is H or halogen;
$R^2$ is $C_{1-4}$-alkyl or $CH_2O$—$C_{1-4}$-alkyl;
$R^3$ is a group A optionally substituted by one or more $R^{3.1}$;
  A is $C_{3-8}$-cycloalkyl or an aromatic or nonaromatic 5 or 6 membered heterocycle containing one or two nitrogen atoms;
  $R^{3.1}$ is $C_{1-4}$-alkyl, $COOR^{3.1.2}$, $C_{1-4}$-alkyl-$COOR^{3.1.2}$, $CH_2R^{3.1.1}$, CONH—$C_{1-4}$-alkyl-$R^{3.1.1}$, COO—$C_{1-4}$-alkyl-$R^{3.1.1}$, OH, O—$C_{1-4}$-alkyl, $NO_2$, $SO_2N(R^{3.1.2})_2$;
  $R^{3.1.1}$ is $NHC_{1-4}$-alkyl, $N(C_{1-4}$-alkyl$)_2$;
  $R^{3.1.2}$ is H or $C_{1-4}$-alkyl;
$R^{3.2}$ is H or $C_{1-4}$-alkyl;

D is $CR^4$ or N $R^4$ is F;

and pharmaceutically acceptable salts thereof.

7. A compound of formula 1 according to claim 1, wherein
$R^1$ is H or F;
$R^2$ is Et or $CH_2OCH_3$
$R^3$ is a group A optionally substituted by one or more $R^{3.1}$;
  A is $C_{3-8}$-cycloalkyl, pyridinyl or pyrazinyl;
  $R^{3.1}$ is $C_{1-4}$-alkyl, $COOR^{3.1.2}$, $C_{1-4}$-alkyl-$COOR^{3.1.2}$, $CH_2R^{3.1.1}$, CONH—$C_{1-4}$-alkyl-$R^{3.1.1}$, COO—$C_{1-4}$-alkyl-$R^{3.1.1}$, OH, O—$C_{1-4}$-alkyl, $NO_2$, $SO_2N(R^{3.1.2})_2$;
  $R^{3.1.1}$ is $NHC_{1-4}$-alkyl, $N(C_{1-4}$-alkyl$)_2$;
  $R^{3.1.2}$ is H or $C_{1-4}$-alkyl;
$R^{3.2}$ is H or $C_{1-4}$-alkyl;

D is $CR^4$ or N $R^4$ is F;

and pharmaceutically acceptable salts thereof.

8. A compound of formula 1 according to claim 1, wherein $R^1$ is H or F;

$R^2$ is Et or $CH_2OCH_3$ $R^3$ is a group A optionally substituted by one or more $R^{3.1}$;

A is $C_{3-8}$-cycloalkyl, pyridinyl or pyrazinyl;

$R^{3.1}$ is $CH_3$, COOH, COOEt, $CH_2COOH$, $CH_2COOEt$, $C(CH_3)_2COOH$, $C(CH_3)_2COOMe$, $CH_2R^{3.1.1}$, COO—$CH_2$—$CH_2$—$R^{3.1.1}$, OH, OMe, $NO_2$, $SO_2NMe_2$;

$R^{3.1.1}$ is $NMe_2$;

$R^4$ is F;

and pharmaceutically acceptable salts thereof.

9. A compound of formula 1 according to claim 1, wherein $R^3$ is

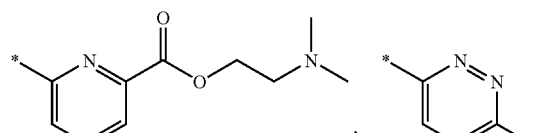

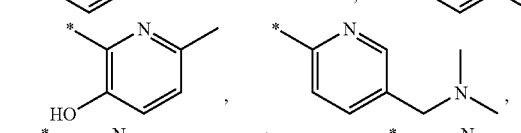

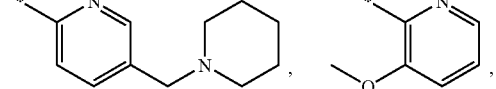

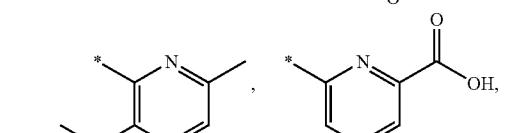

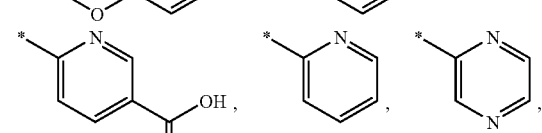

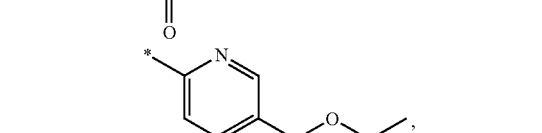

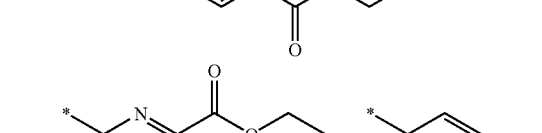

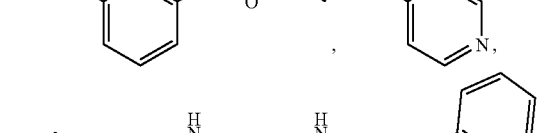

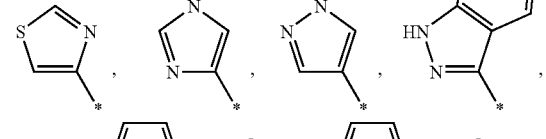

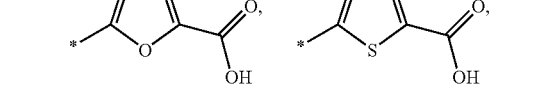

-continued

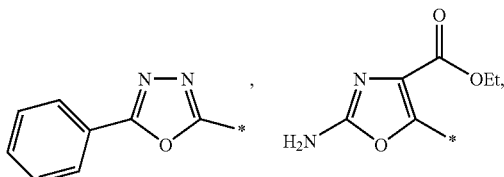

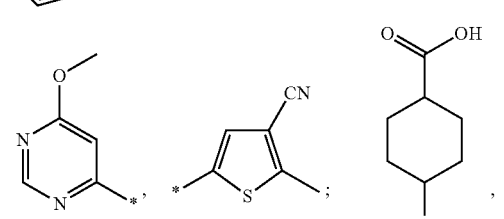

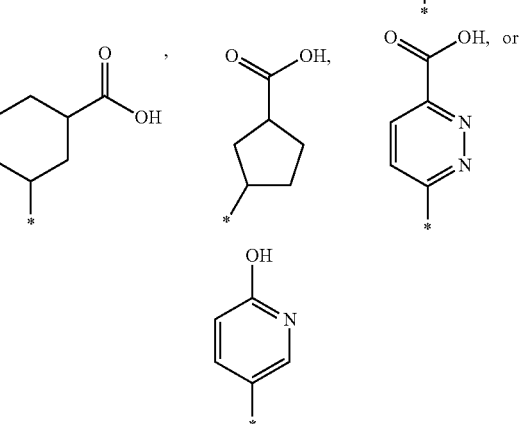

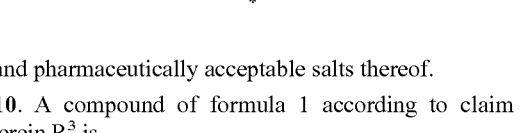

and pharmaceutically acceptable salts thereof.

10. A compound of formula 1 according to claim 1, wherein $R^3$ is

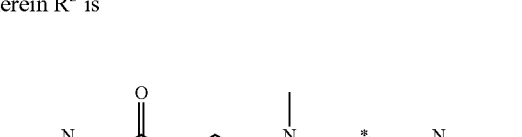

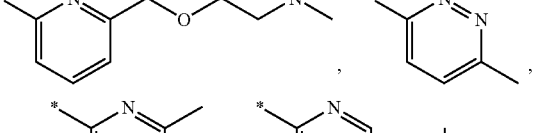

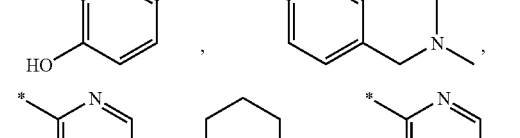

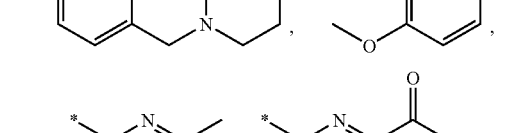

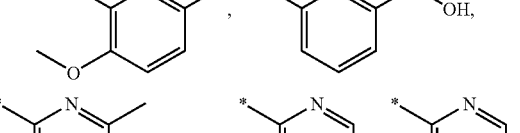

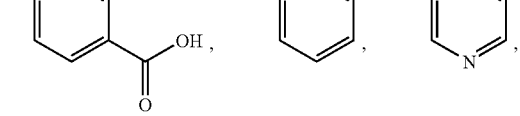

-continued

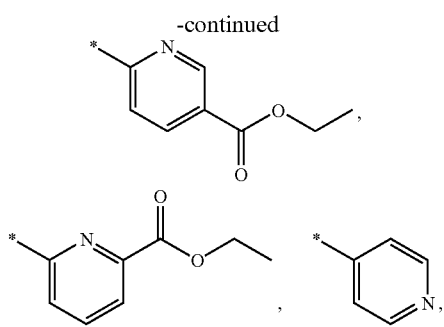

and pharmaceutically acceptable salts thereof.

11. Pharmaceutical composition comprising one or more compounds of formula 1 according to claim 1.

12. A compound of formula 1 according to claim 1 formulated in a therapeutically effective amount with one or more excipients to provide a medicament.

13. A pharmaceutical composition comprising additionally to a compound of formula 1, according to claim 1, a pharmaceutically active compound selected from the group consisting of betamimetics, anticholinergics, corticosteroids, PDE4-inhibitors, LTD4-antagonists, EGFR-inhibitors, dopamin-agonists, antiallergic agents, PAF-antagonists and PI3-kinase inhibitors, or combinations of two or three of these active compounds.

* * * * *